US006172192B1

(12) United States Patent
Jacobs et al.

(10) Patent No.: US 6,172,192 B1
(45) Date of Patent: Jan. 9, 2001

(54) *TOXOPLASMA GONDII* ANTIGEN TG20

(75) Inventors: Dirk Jacobs, Ghent; Eric Saman, Bomem; Hugo Van Heuverswyn, Laarne, all of (BE)

(73) Assignee: Innogenetics N.V., Ghent (BE)

( * ) Notice: Under 35 U.S.C. 154(b), the term of this patent shall be extended for 0 days.

(21) Appl. No.: 09/101,135

(22) PCT Filed: Jan. 27, 1997

(86) PCT No.: PCT/EP97/00394

§ 371 Date: Jun. 30, 1998

§ 102(e) Date: Jun. 30, 1998

(87) PCT Pub. No.: WO97/27300

PCT Pub. Date: Jul. 31, 1997

(30) Foreign Application Priority Data

Jan. 26, 1996 (EP) ................................... 96870006

(51) Int. Cl.[7] ............................. C07K 1/00; C07K 14/00; C07K 17/00; G01N 33/53; G01N 33/531
(52) U.S. Cl. ........................... 530/350; 435/7.1; 435/7.2; 435/7.22; 435/7.92; 435/961; 435/968; 435/973; 435/971; 435/975
(58) Field of Search ............................... 530/350; 435/7.1, 435/7.2, 7.22, 7.92, 961, 968, 973, 971, 975

(56) References Cited

FOREIGN PATENT DOCUMENTS 0 431 541   12/1991   (EP) .

OTHER PUBLICATIONS

Fischer et al. Mol. & Biochem. Parasitol. 91:251–262, 1998.*
Mineo et al, J. Immunol. 151/9: 3951–3964, 1993.*
Darcy et al. Parasitol. Res. 76:473–78, 1990.*
Santoro et al, Parasite Immunol. 8:631–639, 1986.*
Jacobs et al, Mol & Biochem. Parasitol 91: 237–249, 1998.*
Coughlan et al, Parasite Immunol. 17:465–68, 1995.*
Scheerlinck et al Mol. Immunol. 30/8:733–739, 1993.*
Supply et al, Vaccine 17:705–714, 1999.*
Jacobs et al Clin. & Diagnostic Lab. Immunol 6/1:24–29, 1999.*
Hybridoma, vol. 9, No. 5, 1990, pp. 453–463, XP002004716, Saavedra et al.: "Monoclonal antibodies identify new *Toxoplasma gondii* soluble antigens" cited in the application see the whole document.
Database Embl Feb. 29, 1996 XP002031914 see sequences alignmnets & ID: TG9391, AN=N60939, Ajioka et al.: "TgESTzy14f05.rl *Toxoplasma gondii* cDNA clone tgzy14f05.rl 5".

\* cited by examiner

*Primary Examiner*—Nita Minnifield
(74) *Attorney, Agent, or Firm*—Nixon & Vanderhye P.C.

(57) ABSTRACT

The present invention relates to isolated and pure *Toxoplasma gondii* antigenic fragments, recombinant polypeptides, nucleic acids encoding them, primers and probes derived from the same, as well as the use of these polypeptides, nucleic acids, primers and probes in methods and kits for the diagnosis and prevention of *T. gondii* infection in mammals (humans and animals).

31 Claims, 9 Drawing Sheets

Figure 1A:
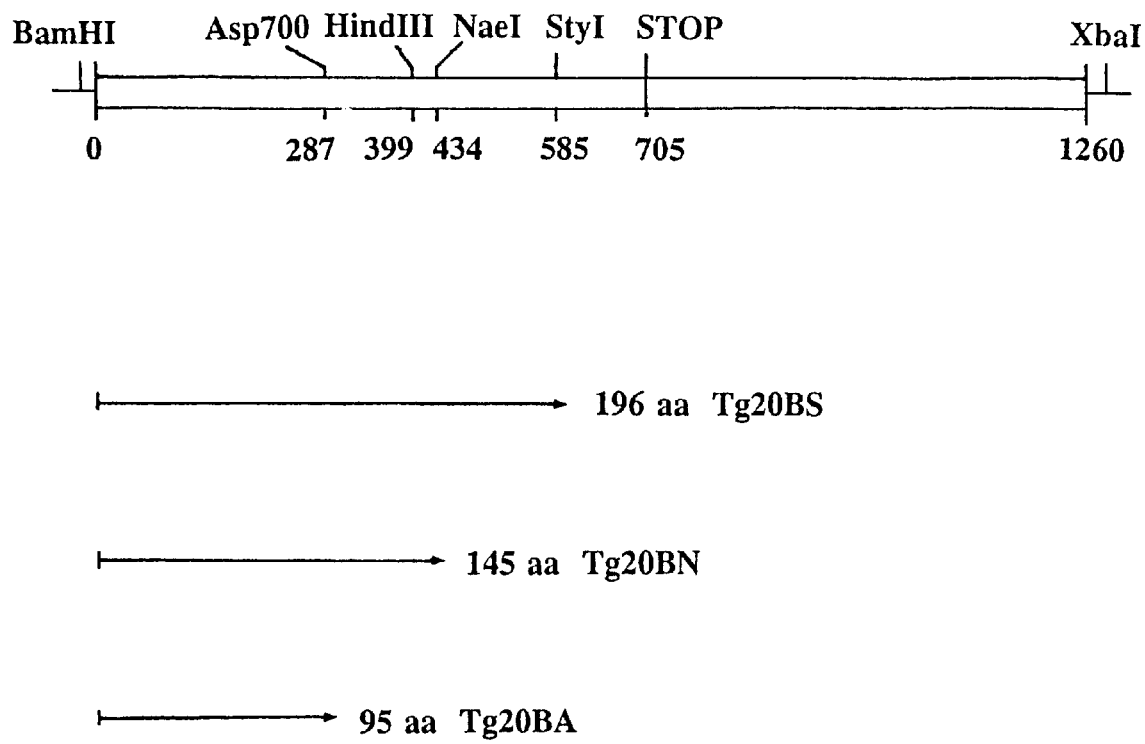

```
         10        20        30        40        50        60
         |         |         |         |         |         |
GAATTCGGCGCAATTTTTTCCGCGCTTTGTGTTTTAGGCCTGGTGGCGGCGGCTTTGCCC
                                                      ↓       ↓
GluPheGlyAlaIlePheSerAlaLeuCysValLeuGlyLeuValAlaAlaAlaLeuPro 70        80        90        100       110       120
         |         |         |         |         |         |
CAGTTCGCTACCGCGGCCACCGCGTCAGATGACGAACTGATGAGTCGAATCCGAAATTCT
                  ↓
GlnPheAlaThrAlaAlaThrAlaSerAspAspGluLeuMETSerArgIleArgAsnSer 130       140       150       160       170       180
         |         |         |         |         |         |
GACTTTTTCGATGGTCAAGCACCCGTTGACAGTCTCAGACCGACGAACGCCGGTGTCGAC

AspPhePheAspGlyGlnAlaProValAspSerLeuArgProThrAsnAlaGlyValAsp 190       200       210       220       230       240
         |         |         |         |         |         |
TCGAAAGGGACCGACGATCACCTCACCACCAGCATGGATAAGGCATCTGTAGAGAGTCAG

SerLysGlyThrAspAspHisLeuThrThrSerMETAspLysAlaSerValGluSerGln 250       260       270       280       290       300
         |         |         |         |         |         |
CTTCCGAGAAGAGAGCCATTGGAGACGGAGCCAGATGAACAAGAAGAAGTTCATTTCAGG
                                          Asp700
LeuProArgArgGluProLeuGluThrGluProAspGluGlnGluGluValHisPheArg 310       320       330       340       350       360
         |         |         |         |         |         |
AAGCGAGGCGTCCGTTCCGACGCTGAAGTGACTGACGACAACATCTACGAGGAGCACACT

LysArgGlyValArgSerAspAlaGluValThrAspAspAsnIleTyrGluGluHisThr
```

Fig. 1B

```
         370       380       390       400       410       420
          |         |         |         |         |         |
GATCGTAAGGTGGTTCCGAGGAAGTCGGAGGGCAAGCGAAGCTTCAAAGACTTGCTGAAG
                                       HindIII
AspArgLysValValProArgLysSerGluGlyLysArgSerPheLysAspLeuLeuLys 430       440       450       460       470       480
          |         |         |         |         |         |
AAGCTCGCGCTGCCGGCTGTTGGTATGGGTGCATCGTATTTTGCCGCTGATAGACTTGTG
             NaeI
LysLeuAlaLeuProAlaValGlyMETGlyAlaSerTyrPheAlaAlaAspArgLeuVal 490       500       510       520       530       540
          |         |         |         |         |         |
CCGGAACTAACAGAGGAGCAACAGAGAGGCGACGAACCCCTAACCACCGGCCAGAATGTG ProGluLeuThrGluGluGlnGlnArgGlyAspGluProLeuThrThrGlyGlnAsnVal 550       560       570       580       590       600
          |         |         |         |         |         |
GGCACTGTGTTAGGCTTCGCAGCGCTTGCTGCTGCCGCAGCGTTCCTTGGCATGGGTCTC
                                          StyI
GlyThrValLeuGlyPheAlaAlaLeuAlaAlaAlaAlaAlaPheLeuGlyMETGlyLeu 610       620       630       640       650       660
          |         |         |         |         |         |
ACGAGGACGTACCGACATTTTCCCCACGCAAAAACAGATCACGGCAGCCTGCACTCGAG ThrArgThrTyrArgHisPheSerProArgLysAsnArgSerArgGlnProAlaLeuGlu 670       680       690       700       710       720
          |         |         |         |         |         |
CAAGAGGTGCCTGAATCAGGCGAAGATGGGGAGGATGCCCGCCAGTAGGATATGGGGGCT GlnGluValProGluSerGlyGluAspGlyGluAspAlaArgGln---

730       740       750       760       770       780
          |         |         |         |         |         |
AATAAAAGTGAGTAGGAGCTCGAGGACAGTGTCCCGAACGCGCCTGAGAGGCAGACAGAC
```

Fig. 1C

```
         790       800       810       820       830       840
          |         |         |         |         |         |
ACAGAAGAGTGAAGAAAAACAACATGGTATTACGTGCGGTGAGTGTTTGCTGTCACGTGT 850       860       870       880       890       900
          |         |         |         |         |         |
TTTTTGCGCCACAAAGACAGCTTGTGTTGTATGCATGGGATCGACAGTTCATGGACGGCG 910       920       930       940       950       960
          |         |         |         |         |         |
CTACCCAGAGAGGCGGCATTTGCGTACACCGTGGGTCGTCATGAGTACCGGGACATCGTG 970       980       990      1000      1010      1020
          |         |         |         |         |         |
TTCGTGTTTATTTGTTCATGTCGAAGTGCACTAAGACACGAGACGAAAGGGTGGTTCCGC 1030      1040      1050      1060      1070      1080
          |         |         |         |         |         |
CCCTGGCAGCATCACGTAGTGGTTTCTTTGTCGAGAACAGCGGCAGTCCGAGGCCACTTG 1090      1100      1110      1120      1130      1140
          |         |         |         |         |         |
AGACAGGATGTTTGAGTGTATACAGACAACGTGGTCACAGCATGAGGCAAAGCTGTCTAA 1150      1160      1170      1180      1190      1200
          |         |         |         |         |         |
GCAGCCATTTGCGCGAGCGAAGTCATCCATGCCGACTGTGTGAGCCTCTTTCGTCACTTT 1210      1220      1230      1240      1250      1260
          |         |         |         |         |         |
GAATGAGACAGAAACTAAGACTCGCAGCAGGTCTGAATATTGCGAATAAAAACCGAATTC
```

Fig. 1D

```
MVRSSSQNSS DKPVAHVVAN HQVEEQGIHH HHHHVDPEFG AIFSALCVLG

LVAAALPQFA TAATASDDEL MSRIRNSDFF DGQAPVDSLR PTNAGVDSKG

TDDHLTTSMD KASVESQLPR REPLETEPDE QEEVHFRKRG VRSDAEVTDD

NIYEEHTDRK VVPRKSEGKR SFKDLLKKLA LPAVGMGASY FAADRLVPEL

TEEQQRGDEP LTTGQNVGTV LGFAALAAAA AFLGMGLTRT YRHFSPRKNR

SRQPALEQEV PESGEDGEDA RQ
```

Fig. 4

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
       (A) LENGTH: 1260 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 1..708

(ix) FEATURE:
       (A) NAME/KEY: mat_peptide
       (B) LOCATION: 1..705

(xi) SEQUENCE DESCRIPTION: SEQ ID NO: 1:

```
GAA TTC GGC GCA ATT TTT TCC GCG CTT TGT GTT TTA GGC CTG GTG GCG      48
Glu Phe Gly Ala Ile Phe Ser Ala Leu Cys Val Leu Gly Leu Val Ala
 1               5                  10                  15

GCG GCT TTG CCC CAG TTC GCT ACC GCG GCC ACC GCG TCA GAT GAC GAA      96
Ala Ala Leu Pro Gln Phe Ala Thr Ala Ala Thr Ala Ser Asp Asp Glu
             20                  25                  30

CTG ATG AGT CGA ATC CGA AAT TCT GAC TTT TTC GAT GGT CAA GCA CCC     144
Leu Met Ser Arg Ile Arg Asn Ser Asp Phe Phe Asp Gly Gln Ala Pro
         35                  40                  45

GTT GAC AGT CTC AGA CCG ACG AAC GCC GGT GTC GAC TCG AAA GGG ACC     192
Val Asp Ser Leu Arg Pro Thr Asn Ala Gly Val Asp Ser Lys Gly Thr
     50                  55                  60

GAC GAT CAC CTC ACC ACC AGC ATG GAT AAG GCA TCT GTA GAG AGT CAG     240
Asp Asp His Leu Thr Thr Ser Met Asp Lys Ala Ser Val Glu Ser Gln
 65                  70                  75                  80

CTT CCG AGA AGA GAG CCA TTG GAG ACG GAG CCA GAT GAA CAA GAA GAA     288
Leu Pro Arg Arg Glu Pro Leu Glu Thr Glu Pro Asp Glu Gln Glu Glu
             85                  90                  95

GTT CAT TTC AGG AAG CGA GGC GTC CGT TCC GAC GCT GAA GTG ACT GAC     336
Val His Phe Arg Lys Arg Gly Val Arg Ser Asp Ala Glu Val Thr Asp
            100                 105                 110

GAC AAC ATC TAC GAG GAG CAC ACT GAT CGT AAG GTG GTT CCG AGG AAG     384
Asp Asn Ile Tyr Glu Glu His Thr Asp Arg Lys Val Val Pro Arg Lys
        115                 120                 125

TCG GAG GGC AAG CGA AGC TTC AAA GAC TTG CTG AAG AAG CTC GCG CTG     432
Ser Glu Gly Lys Arg Ser Phe Lys Asp Leu Leu Lys Lys Leu Ala Leu
    130                 135                 140

CCG GCT GTT GGT ATG GGT GCA TCG TAT TTT GCC GCT GAT AGA CTT GTG     480
Pro Ala Val Gly Met Gly Ala Ser Tyr Phe Ala Ala Asp Arg Leu Val
145                 150                 155                 160

CCG GAA CTA ACA GAG GAG CAA CAG AGA GGC GAC GAA CCC CTA ACC ACC     528
Pro Glu Leu Thr Glu Glu Gln Gln Arg Gly Asp Glu Pro Leu Thr Thr
                165                 170                 175

GGC CAG AAT GTG GGC ACT GTG TTA GGC TTC GCA GCG CTT GCT GCT GCC     576
Gly Gln Asn Val Gly Thr Val Leu Gly Phe Ala Ala Leu Ala Ala Ala
            180                 185                 190

GCA GCG TTC CTT GGC ATG GGT CTC ACG AGG ACG TAC CGA CAT TTT TCC     624
Ala Ala Phe Leu Gly Met Gly Leu Thr Arg Thr Tyr Arg His Phe Ser
        195                 200                 205
```

```
CCA CGC AAA AAC AGA TCA CGG CAG CCT GCA CTC GAG CAA GAG GTG CCT    672
Pro Arg Lys Asn Arg Ser Arg Gln Pro Ala Leu Glu Gln Glu Val Pro
    210                 215                 220

GAA TCA GGC GAA GAT GGG GAG GAT GCC CGC CAG TAGGATATGG GGGCTAATAA  725
Glu Ser Gly Glu Asp Gly Glu Asp Ala Arg Gln
225                 230                 235

AAGTGAGTAG GAGCTCGAGG ACAGTGTCCC GAACGCGCCT GAGAGGCAGA CAGACACAGA  785

AGAGTGAAGA AAAACAACAT GGTATTACGT GCGGTGAGTG TTTGCTGTCA CGTGTTTTTT  845

GCGCCACAAA GACAGCTTGT GTTGTATGCA TGGGATCGAC AGTTCATGGA CGGCGCTACC  905

CAGAGAGGCG GCATTTGCGT ACACCGTGGG TCGTCATGAG TACCGGGACA TCGTGTTCGT  965

GTTTATTTGT TCATGTCGAA GTGCACTAAG ACACGAGACG AAAGGGTGGT TCCGCCCCTG 1025

GCAGCATCAC GTAGTGGTTT CTTTGTCGAG AACAGCGGCA GTCCGAGGCC ACTTGAGACA 1085

GGATGTTTGA GTGTATACAG ACAACGTGGT CACAGCATGA GGCAAAGCTG TCTAAGCAGC 1145

CATTTGCGCG AGCGAAGTCA TCCATGCCGA CTGTGTGAGC CTCTTTCGTC ACTTTGAATG 1205

AGACAGAAAC TAAGACTCGC AGCAGGTCTG AATATTGCGA ATAAAAACCG AATTC      1260
```

(2) INFORMATION FOR SEQ ID NO: 2:

(i) SEQUENCE CHARACTERISTICS:
        (A) LENGTH: 235 amino acids
        (B) TYPE: amino acid
        (D) TOPOLOGY: linear (ii) MOLECULE TYPE: protein (xi) SEQUENCE DESCRIPTION: SEQ ID NO: 2:

```
Glu Phe Gly Ala Ile Phe Ser Ala Leu Cys Val Leu Gly Leu Val Ala
 1               5                  10                  15

Ala Ala Leu Pro Gln Phe Ala Thr Ala Ala Thr Ala Ser Asp Asp Glu
            20                  25                  30

Leu Met Ser Arg Ile Arg Asn Ser Asp Phe Phe Asp Gly Gln Ala Pro
        35                  40                  45

Val Asp Ser Leu Arg Pro Thr Asn Ala Gly Val Asp Ser Lys Gly Thr
    50                  55                  60

Asp Asp His Leu Thr Thr Ser Met Asp Lys Ala Ser Val Glu Ser Gln
65                  70                  75                  80

Leu Pro Arg Arg Glu Pro Leu Glu Thr Glu Pro Asp Glu Gln Glu Glu
                85                  90                  95

Val His Phe Arg Lys Arg Gly Val Arg Ser Asp Ala Glu Val Thr Asp
            100                 105                 110

Asp Asn Ile Tyr Glu Glu His Thr Asp Arg Lys Val Val Pro Arg Lys
        115                 120                 125

Ser Glu Gly Lys Arg Ser Phe Lys Asp Leu Leu Lys Lys Leu Ala Leu
    130                 135                 140

Pro Ala Val Gly Met Gly Ala Ser Tyr Phe Ala Ala Asp Arg Leu Val
145                 150                 155                 160

Pro Glu Leu Thr Glu Glu Gln Gln Arg Gly Asp Glu Pro Leu Thr Thr
                165                 170                 175

Gly Gln Asn Val Gly Thr Val Leu Gly Phe Ala Ala Leu Ala Ala Ala
            180                 185                 190

Ala Ala Phe Leu Gly Met Gly Leu Thr Arg Thr Tyr Arg His Phe Ser
        195                 200                 205

Pro Arg Lys Asn Arg Ser Arg Gln Pro Ala Leu Glu Gln Glu Val Pro
```

```
              210                 215                 220
Glu Ser Gly Glu Asp Gly Glu Asp Ala Arg Gln
225                 230                 235

(2) INFORMATION FOR SEQ ID NO: 3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Glu Pro Asp Glu Gln Glu Glu Val His Phe Arg Lys Arg Gly Val Arg
1               5                   10                  15

Ser Asp Ala Glu
            20

(2) INFORMATION FOR SEQ ID NO: 4:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Arg Lys Arg Gly Val Arg Ser Asp Ala Glu Val Thr Asp Asp Asn Ile
1               5                   10                  15

Tyr Glu Glu His
            20

(2) INFORMATION FOR SEQ ID NO: 5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Val Thr Asp Asp Asn Ile Tyr Glu Glu His Thr Asp Arg Lys Val Val
1               5                   10                  15

Pro Arg Lys Ser
            20

(2) INFORMATION FOR SEQ ID NO: 6:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Thr Asp Arg Lys Val Val Pro Arg Lys Ser Glu Gly Lys Arg Ser Phe
1               5                   10                  15

Lys Asp Leu Leu
```

20

(2) INFORMATION FOR SEQ ID NO: 7:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 7:

```
Glu Gly Lys Arg Ser Phe Lys Asp Leu Leu Lys Lys Leu Ala Leu Pro
 1               5                  10                  15
```

(2) INFORMATION FOR SEQ ID NO: 8:

(i) SEQUENCE CHARACTERISTICS:
      (A) LENGTH: 272 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 8:

```
Met Val Arg Ser Ser Ser Gln Asn Ser Ser Asp Lys Pro Val Ala His
 1               5                  10                  15

Val Val Ala Asn His Gln Val Glu Glu Gln Gly Ile His His His His
                20                  25                  30

His His Val Asp Pro Glu Phe Gly Ala Ile Phe Ser Ala Leu Cys Val
            35                  40                  45

Leu Gly Leu Val Ala Ala Ala Leu Pro Gln Phe Ala Thr Ala Ala Thr
50                  55                  60

Ala Ser Asp Asp Glu Leu Met Ser Arg Ile Arg Asn Ser Asp Phe Phe
65                  70                  75                  80

Asp Gly Gln Ala Pro Val Asp Ser Leu Arg Pro Thr Asn Ala Gly Val
                85                  90                  95

Asp Ser Lys Gly Thr Asp Asp His Leu Thr Thr Ser Met Asp Lys Ala
            100                 105                 110

Ser Val Glu Ser Gln Leu Pro Arg Arg Glu Pro Leu Glu Thr Glu Pro
        115                 120                 125

Asp Glu Gln Glu Glu Val His Phe Arg Lys Arg Gly Val Arg Ser Asp
    130                 135                 140

Ala Glu Val Thr Asp Asp Asn Ile Tyr Glu Glu His Thr Asp Arg Lys
145                 150                 155                 160

Val Val Pro Arg Lys Ser Glu Gly Lys Arg Ser Phe Lys Asp Leu Leu
                165                 170                 175

Lys Lys Leu Ala Leu Pro Ala Val Gly Met Gly Ala Ser Tyr Phe Ala
            180                 185                 190

Ala Asp Arg Leu Val Pro Glu Leu Thr Glu Gln Gln Arg Gly Asp
        195                 200                 205

Glu Pro Leu Thr Thr Gly Gln Asn Val Gly Thr Val Leu Gly Phe Ala
    210                 215                 220

Ala Leu Ala Ala Ala Ala Phe Leu Gly Met Gly Leu Thr Arg Thr
225                 230                 235                 240

Tyr Arg His Phe Ser Pro Arg Lys Asn Arg Ser Arg Gln Pro Ala Leu
                245                 250                 255
```

-continued

```
Glu Gln Glu Val Pro Glu Ser Gly Glu Asp Gly Glu Asp Ala Arg Gln
            260                 265                 270
```

TOXOPLASMA GONDII ANTIGEN TG20

This application is a 371 of PCT/EP97/00394 filed Jan. 27, 1997.

The present invention relates to isolated and pure *Toxoplasma gondii* antigenic fragments, recombinant polypeptides, nucleic acids encoding them, primers and probes derived from the same, as well as the use of these polypeptides, nucleic acids, primers and probes in methods and kits for the diagnosis and prevention of *T. gondii* infection in mammals (humans and animals).

*Toxoplasma gondii* is an ubiquitous intracellular protozoan parasite which infects mammals and birds. Although toxoplasmosis is in general clinically asymptomatic in healthy individuals, it may cause severe complications in pregnant women and immunocompromised patients. If primary infection occurs during pregnancy, transplacental transmission can lead to abortion or neonatal malformations (for reviews see Remington and Krahenbuhl, 1982; Hughes, 1985). In AIDS patients, Toxoplasma is recognized as a major opportunistic pathogen. In such immunodeficient individuals, rupture of cysts which persist in the tissues of the host after a primary infection and release of proliferative forms of the parasite may cause severe disseminated toxoplasmosis and/or encephalitis. In approximately 30 percent of Toxoplasma-antibody-positive patients with AIDS, toxoplasmic encephalitis will develop due to reactivation of their latent infection.

The fetus and the newborn are very sensitive to toxoplasmosis. Infection of the mother during pregnancy and transmission to the fetus can lead to miscarriage, birth of abnormal children (especially with ocular and cerebral lesions), or birth of apparently normal children who will develop grave sequaelae months or years later (blindness, mental retardation). Current estimates indicate that 0.1 to 0.9% of newborns are afflicted with congenital toxoplasmosis.

Besides its negative impact on human health, the parasite is also detrimental in sheep and pig farming since abortions resulting from the infection lead to relatively important economic losses (Beverly, 1976).

In the absence of efficient profylactic measures, there is a high necessity for early, sensitive and specific diagnosis.

In response to infection, immunocompetent hosts mount an immune response, which involves both humoral and cellular components (Remington and Krahenbuhl, 1982). The immune response confers protection against subsequent infection of the host: women showing serological evidence of previous infection before the onset of pregnancy are at no risk of transmitting toxoplasmosis to their fetus. In-vitro and in-vivo studies have indicated that cell-mediated immunity plays an essential role in protection and have identified interferon-gamma (IFN-gamma) as the major mediator of resistance (Frenkel, 1967; Nathan et al., 1984; Pfefferkorn, 1984; Sethi et al., 1985; Suzuki and Remington, 1988; Suzuki et al., 1988; Suzuki and Remington, 1990; Gazinelli et al., 1991).

The humoral component underlies the methods generally used in toxoplasmosis diagnosis. Like in other infectious diseases IgM class antibodies appear before IgG class antibodies. This difference is used to know whether a pregnant woman has an acute or chronic phase infection, only the former being dangerous for fetal transmission. However, in a number of cases IgM class antibodies remain high for a longer than usual time period, making a differential diagnosis difficult.

The reference tests in Toxoplasma diagnosis are the Toxoplasma lysis test (TLT) and the immunofluorescence test (IF). The detection of antibodies against Toxoplasma is most often carried out by an Enzyme Linked Immunoassay (ELISA) or tests based on the same principle. The specificity and sensitivity of these tests is not always optimal and depend on the quality of the antigen preparation used. Most often the antigen used is a fraction of a total cell lysate, lacking sufficient specificity.

The use of a selection of well characterised *Toxoplasma gondii* recombinant antigens could furnish better tools for a Toxoplasma diagnostic assay.

Several antigens of Toxoplasma have already been cloned and expressed as recombinant antigens. Several excreted/secreted antigens have been shown to be recognized by sera from patients: GRA1 (23 kDa) (Cesbron-Delauw et al, 1989; EP-A-0 346 430), GRA2 (28.5 or 28 kDa) (Mercier et al, 1993; S. F. Parmley et al, 1993; WO 93/25689), GRA6 (Lecordier et al, 1995), as well as some other cellular antigens, like SAG2 (P22) (Parmley et al, 1992), SAG1 (P30) (Kim et al, 1994), ROP2 (54 kDa) (Van Gelder et al, 1993) and a number of *T. gondii* antigenic fragments as described e.g. in EP-A-0 431 541 (Behringwerke).

A vaccine for controlling this infectious agent would be of great value and the feasibility of its development is suggested by the fact that primary infection with Toxoplasma results in specific and long lasting immunity against reinfection (Remington and Kranenbuhl, 1982). However, no effective and safe vaccine is currently available against toxoplasmosis in humans. A live temperature-sensitive mutant of the highly virulent RH strain, can induce protective immunity in mice and hamsters. This mutant, names ts-4 does not persist in the host, as it cannot form bradyzoites and cysts (Waldeland and Frenkel, 1983; McLeod et al., 1988; Suzuki and Remington, 1990). Since 1988, a live vaccine is available for sheep. It consists of *T. gondii* tachyzoites of the S48 incomplete strain grown on tissue culture (Toxovax, Ministry of Agriculture and Fisheries, New Zealand). By passing through laboratory mice the strain lost the ability to develop bradyzoites (cysts). This vaccine protects naive sheep against an infect with *T. gondii* (Buxton, 1991, 1993).

The aim of the present invention is to provide new polypeptides and peptides useful in the diagnosis and/or profylaxis of *Toxoplasma gondii* infection in mammals.

It is more particularly an aim of the invention to provide polypeptides and peptides useful in the serodiagnosis of *T. gondii* infection, and possibly enabling discrimination between chronic and acute infection.

It is in addition an aim of the present invention to provide polypeptides and peptides useful in diagnostic assay for *T. gondii* infection based on the cellular immune response of the infected host.

It is moreover an aim of the present invention to provide for polypeptides and peptides useful in a vaccine preparation against *T. gondii* infection.

It is a specific aim of the present invention to provide purified and isolated Tg20 antigenic fragments.

More specifically, it is an aim of the invention to provide recombinant Tg20 antigenic fragments.

It is moreover an aim of the invention to provide the amino acid sequence of Tg20 antigenic fragments, and nucleic acid sequences coding for the same.

It is moreover an aim of the invention to provide for monoclonal and polyclonal antibodies specifically reacting with antigenic fragments of the Tg20 protein.

It is also an aim of the present invention to provide for primers specifically amplifying Tg20 nucleic acid sequences, as well as probes specifically hybridizing with Tg20 nucleic acid sequences.

It is another aim of the invention to provide for diagnostic methods and/or kits for *T. gondii* infection, using the above-mentioned Tg20 polypeptides, peptides, antibodies, primers and/or probes as one of the active principles.

It is in particular an aim of the present invention to provide for a serodiagnostic method or kit for *T. gondii* infection, whereby the active principle comprises the Tg20 polypeptides or peptides of the invention in combination with other *T. gondii* antigens, more particularly, in combination with the Tg34 antigen (=Rop2 antigen), or fragments thereof, as described by Van Gelder et al. (1993).

It is finally an aim of the present invention to provide for a vaccine composition for providing protective immunity against *T. gondii* infection in mammals, more particularly in humans and/or domesticated animals.

All of the above-mentioned aims have been achieved by the following embodiments of the invention.

As described in more detail in the examples section, the current invention describes the identification and sequencing of an antigenic fragment of *T. gondii*. Said antigenic fragment was selected from a λgt11 expression library of *T. gondii* (clone Tg20), on the basis of its reactivity with a number of sera from *T. gondii* infected patients, which were previously shown not to react with other *T. gondii* antigens, like the Tg34 (Rop2) antigen, or fragments thereof (Van Gelder et al. 1993).

As described above, there is a current need to replace crude *T. gondii* antigen preparations used in actual diagnostic assays, by a selection of well-defined isolated antigenic (poly)peptides. The Tg20 polypeptides and peptides of the current invention are ideal candidates to be included in such "new generation" diagnostic assays, due to their high specificity and sensitivity in detecting *T. gondii* infected individuals, as described further in the examples section. Moreover, the Tg20 polypeptides have been selected such that they show a complementary reactivity pattern with other *T. gondii* antigenic fragments, which have already been described to be useful in diagnostics of toxoplasmosis, like the Tg34 antigen (Van Gelder et al. 1993). Tg20 and Tg34 antigenic polypeptides are therefore particularly suitable to be used in combination with each other in a diagnostic assay.

The invention thus relates to a polypeptide or peptide containing (1) an amino acid sequence extending from amino acid position x to amino acid y in the sequence as shown in FIG. 1*b* (SEQ ID NO 2), with x=1 and y=196, and/or
x=1 and y=160, and/or
x=1 and y=145, and/or
x=95 and y=145, and/or (2) any fragment of (1), with said fragment comprising a stretch of at least 7 contiguous amino acids of the sequence as defined in (1), and/or (3) any equivalents of (1) or (2) originating from the substitution of one or several amino acids in the sequence of (1) or (2), with said polypeptides or peptides containing a reactive epitope important in the humoral and/or cell-mediated immune response of the *T. gondii* infected host organism.

Fragments of the above-mentioned polypeptides should contain at least 7 contiguous amino acids, possibly also a stretch of 8, 9, 10, 11, 12, 13, 14, 15, 16, 17, 18, 19, 20, 21, 22, 23, 24, 25, 30, 50 or more contiguous amino acids selected from the amino acid sequence extending from position 1 to position 196 as represented in FIG. 1*b* (SEQ ID NO 2).

Figure 6:
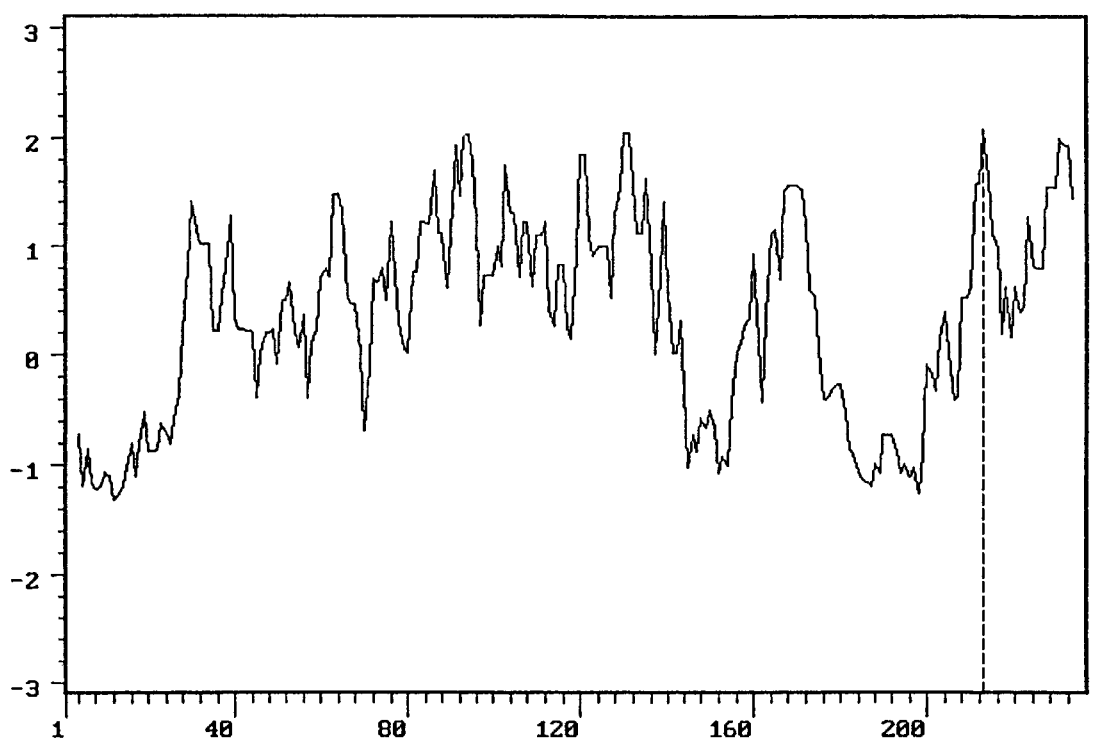

Polypeptide fragments containing an epitope important in the serological response of an individual infected by *T. gondii* may be selected form a hydrophylicity plot of the antigen, according to principles known to the person skilled in the art. The hydrophylicity plot of the Tg20 antigen of the invention (SEQ ID NO 2) is represented in FIG. 6. The experimental data in the examples section show that the most immunodominant epitopes of the Tg20 antigen are located in the aminoterminal part of the antigen, i.e. from amino acid position 1 to amino acid position 196, and more particularly in the region extending from position 95 to position 145 of the sequence as represented in FIG. 1. From the hydrophylicity plot of this Tg20 antigen (FIG. 6) it is clear however that additional epitopes may be located in the C-terminal part of the protein, e.g. in the region extending from amino acid position 197 to amino acid position 235, more particularly in the region extending from position 205 to position 220.

The term "polypeptide" designates a linear series of amino acids connected one to the other by peptide bonds between the alpha-amino and carboxy groups of adjacent amino acids. Polypeptides with a length of twenty five amino acids or less can also be named "peptides". Polypeptides can show a variety of lengths, either in their natural (uncharged) forms or in forms which are salts, and either free of modifications such as glycosylation, side chain oxidation, or phosphorylation or containing these modifications. It is well understood in the art that amino acid sequences contain acidic and basic groups, and that the particular ionization state exhibited by the peptide is dependent on the pH of the surrounding medium when the protein is in solution, or that of the medium from which it was obtained if the protein is in solid form. Also included in the definition are proteins modified by additional substituents attached to the amino acids side chains, such as glycosyl units, lipids, or inorganic ions such as phosphates, as well as modifications relating to chemical conversions of the chains, such as oxidation of sulfhydryl groups.

It is to be understood that the polypeptides and peptides as described in the current invention can also be extended at one or both of their extremities by so called "linker" sequences, consisting of one or several amino acids (or other molecules, like e.g. biotine), and providing additional physiochemical properties to the (poly)peptide, which may be particularly desirable for certain processes, like e.g. purification, coating and presentation of the (poly)peptide.

A special type of "linker" sequence is the addition of a biotin molecule to the (poly)peptides of the invention. The biotin molecule may be incorporated in the polypeptide sequence either during or after polypeptide synthesis, and may be located N-terminal, or C-terminal or internal of the polypeptide sequence. The biotinylation is especially advantageous when the above-mentioned polypeptides are used in serodiagnostic assays: the presence of biotin in the (poly) peptide molecule facilitates its adhesion and presentation on membranes or plates coated with a biotin binding molecule (like e.g. streptavidin).

Thus, "polypeptide" or its equivalent terms is intended to include the appropriate amino acid sequence referenced, subject to those of the foregoing modifications which do not destroy its functionality.

The polypeptides of the invention, and particularly the peptides, can be prepared by classical chemical synthesis.

The synthesis can be carried out in homogeneous solution or in solid phase.

For instance, the synthesis technique in homogeneous solution which can be used is the one described by Houbenweyl in the book entitled "Methoden de Organischen Chemie" (Methods of Organic Chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL press, Oxford, 1989).

The polypeptides according to this invention can also be prepared by means of recombinant DNA techniques as described by Maniatis et al., Molecular Cloning: A Laboratory Manual, New York, Cold Spring Harbor Laboratory, 1982). The term "recombinant polypeptides" refers to a polypeptide produced by genetic engineering, through transcription and translation of a corresponding DNA sequence under the appropriate regulation elements within an efficient cellular host.

The polypeptides of the invention can also be prepared by isolation and purification from their naturally occurring environment e.g. by purification from *T. gondii* lysates or extracts. The techniques to be used for purification of the polypeptides of the invention are known in the current art of protein purification.

The term "epitope" or "antigenic determinant" refers to a specific region of an antigenic molecule that binds to an antibody (B-cell epitope) or to a T-cell receptor (T-cell epitope).

The term "humoral immune response" refers to the immune response mediated by antibodies, while "cell mediated immune response" is mediated by T-lymphocytes. In the case of *T. gondii* infection, most diagnostic assays are based upon the measurement of the humoral immune response (e.g. serodiagnosis), while protection towards the disease is basically mediated by the cell-mediated immune response. Therefore, it can be said that B-cell epitopes will be important components of a diagnostic assay, while T-cell epitopes will be indispensable in the composition of a vaccine.

As shown in the Examples section, the above-mentioned polypeptides and peptides are selected such that they show a reactivity with sera from *T. gondii* infected individuals and/or stimulate *T. gondii* reactive T-cells.

The term "equivalents" (or "muteins") as specified above, may be defined as polypeptides and peptides containing substitutions of one or several amino acids, provided that said equivalents have retained the immunogenic/antigenic properties of the original polypeptide. An overview of the amino acid substitutions which could form the basis for such equivalents is shown in Table 1. It should be evident that such equivalents may have a slightly different molecular weight from the original sequence as determined by SDS-PAGE.

Said "muteins" may be the result of strain to strain variations of the *Toxoplasma gondii* Tg20 antigen, or may be the result of modifications introduced in the original polypeptide sequences, said modifications bringing about a desirable side effect to the polypeptide molecule (e.g. better physiochemical properties, more efficient purification, more efficient coating characteristics, more stable etc . . . ).

In a more specific embodiment, the invention relates to a polypeptide or peptide containing (1) the amino acid sequence extending from position 95 to position 145 of the sequence in FIG. 1*b* (SEQ ID NO 2), and/or (2) any fragments of (1), with said fragments comprising a stretch of at least 7 contiguous amino acids of the sequence in (1), and/or (3) at least one of the amino acid sequences represented by GluProAspGluGlnGluGluValHis-PheArgLysArgGlyValArgSerAspAlaGlu (SEQ ID NO 3), or ArgLysArgGlyValArgSerAspAla-GluValThrAspAspAsnIleTyrGluGluHis (SEQ ID NO 4), or ValThrAspAspAsnIleTyrGluGlu-HisThrAspArgLysValValProArgLysSer (SEQ ID NO 5), or ThrAspArgLysValValProAr-gLysSerGluSlyLysArgSerPheLysAspLeuLeu (SEQ ID NO 6), or GluGlyLysArgSerPheLysAs-pLeuLeuLysLysLeuAlaLeuPro (SEQ ID NO 7) and/or (4) any equivalents of (1), (2) or (3) originating from the substitution of one or several amino acids in the sequences of (1), (2) or (3), with said polypeptides and peptides containing a reactive epitope important in the humoral and/or cell-mediated immune response of the *T. gondii* infected host organism.

Preferably, the above-mentioned polypeptides and their fragments and/or equivalents are reactive with sera from *T. gondii* infected individuals.

Another embodiment of the invention encompasses a fusion protein consisting of one of the polypeptide sequences as defined above, linked to a heterologous polypeptide sequence.

The term "heterologous polypeptide sequence" refers to any polypeptide sequence other than the Tg20 sequence itself, and may originate from *T. gondii* or from another organism.

A fusion protein may have advantageous effects over the non-fusion polypeptides, said effects being e.g.

a more efficient expression level in a recombinant host (e.g. mTNF fusion protein as exemplified further) and/or, a more easy purification system (e.g. polyhistidine tail as exemplified further) and/or, a combination of several epitopes, originating from different *T. gondii* antigens and/or, a more efficient presentation of the epitopes.

Said fusion protein may be made by recombinant DNA technology, whereby different coding regions are operably linked to each other and expressed in a suitable host cell. Fusion proteins may however also be prepared according to other methods, like in vitro coupling techniques, or chemical synthesis.

The invention also relates to nucleic acids containing (1) a polynucleic acid sequence encoding any of the polypeptides as defined above, and/or (2) a polynucleic acid sequence extending from position x to position y of the polynucleic acid sequence as represented in FIG. 1*b* (SEQ ID NO 1) with x=1 and y=589, and/or x=1 and y=480, and/or x=1 and y=434, and/or x=95 and y=434, and/or (3) a polynucleic acid sequence which is degenerate as a result of the genetic code to the polynucleic acid sequence of (1) or (2), and which still encodes any of the polypeptides as defined above, and/or (4) a polynucleic acid sequence which hybridizes with any of the polynucleic acid sequences as defined in (1) to (3), and/or (5) a fragment of any of the polynucleic acid sequences defined in (1) to (4), said fragment containing a stretch of at least 10, and preferably 11, 12, 13, 14, 15 or more contiguous nucleotides from any of the polynucleic acid sequences as defined in (1) to (3).

The term "nucleic acid" or "polynucleic acid" corresponds to either double-stranded or single-stranded cDNA or genomic DNA or RNA, containing at least 10, 20, 30, 40 or 50 contiguous nucleotides. A nucleic acid which is smaller than 100 nucleotides in length is often also referred to as an oligonucleotide. Single stranded polynucleic acid sequences are always represented in the current invention from the 5' end to the 3' end. It is to be understood however that the complementary sequences, and double stranded sequences are of course also encompassed by the formula used for presentation.

The term "hybridize to" refers to preferably stringent hybridization conditions, allowing hybridization between sequences showing at least 70%, 80%, 90%, 95% or more homology with each other.

The term "degenerate" refers to possible variations in the polynucleic acid sequence encoding the same protein, due to the possible occurrence of different codons for the same amino acid.

According to another embodiment, the present invention relates to an oligonucleotide comprising in its sequence at least 10 contiguous nucleotides which form part of any of the polynucleic acid sequences as defined above, for use as a specific hybridization probe for detecting the polynucleic acids of the invention.

The term "probe" refers to single stranded sequence-specific oligonucleotides which have a sequence which is sufficiently complementary to hybridize to the target sequence to be detected.

Probes according to this aspect of the present invention may be chosen according to any of the techniques known in the art.

Preferably, these probes are about 10 to 50 nucleotides long, more preferably from about 15 to 25 nucleotides.

It should be understood that the probe sequences of the invention may be slightly modified, e.g. by adding or deleting one or a few nucleotides at the extremities (3' or 5') or by substituting some non-essential nucleotides by others (including modified nucleotides and inosine), on condition that these modifications do not alter the specificity of the probes. These modifications may be necessary or desirable e.g. to obtain a higher sensitivity (e.g. because of strain variability of the sequences) or to obtain a sufficient specificity under modified hybridization conditions (buffer, temperature, salt concentration . . . ). Also, changing the amount (concentration) of probe used may be beneficial to obtain more specific hybridization results. It should be noted in this context, that probes of the same length, regardless of their GC content, will hybridize specifically at approximately the same temperature in TMACl solutions (Jacobs et al., 1988).

The latter implies that variant probes contemplated within this aspect of the present invention can be defined as probes hybridizing with the same specificity as the probe they are derived from under stringent hybridization and wash conditions, which may be different or the same as the conditions used for the original probes.

The term "complement" refers to a nucleotide sequence which is exactly complementary to an indicated sequence and which is able to hybridize to the indicated sequences.

According to another embodiment, the present invention relates to an oligonucleotide, comprising in its sequence at least 10 contiguous nucleotides which form part of any of the polynucleic acid sequences as defined above, for use as a primer for specifically amplifying any of the polynucleic acid sequences of the invention.

The term "primer" refers to a single stranded DNA oligonucleotide sequence capable of acting as a point of initiation for synthesis of an extension product which is complementary to the nucleic acid strand to be copies. The length and the sequence of the primer must be such that they allow to prime the synthesis of the extension products. Preferably the primer is about 10–50 nucleotides long, more preferably 10–30 nucleotides long. Specific length and sequence will depend on the complexity of the required DNA or RNA targets, as well as on the conditions of primer use such as temperature and ionic strength.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules using primer extension. During amplification, the amplified products can be conveniently labelled either using labelled primers or by incorporating labelled nucleotides. Labels may be isotopic ($^{32}$P, $^{35}$S, etc.) or non-isotopic (biotin, digoxigenin, etc.). The amplification reaction is repeated between 20 and 80 times, advantageously between 30 and 50 times.

The oligonucleotides used as primers or probes may also contain or consist of nucleotide analoges such as phosphorothioates (Matsukura et al., 1987), alkylphosphoro-thiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention, these variations will necessitate adaptions with respect to the conditions under which the oligonucleotide should be used to obtain the required specificity and sensitivity. However, the eventual results of hybridization will be essentially the same as those obtained with the unmodified oligonucleotides.

The introduction of these modifications may be advantageous in order to positively influence characteristics such as hybridization kinetics, reversibiltiy of the hybrid-formation, biological stability of the oligonucleotide molecules, etc.

Another embodiment of the invention provides for recombinant nucleic acids comprising any of the above-mentioned nucleic acids for cloning and/or expression purposes.

The term "recombinant nucleic acid" refers to a nucleic acid molecule which has been made in vitro by recombinant techniques, and which may contain nucleic acids originating from different sources ligated to each other.

In particular, the invention provides for a recombinant vector into which one of the above-mentioned nucleic acids has been inserted for cloning and/or expression purposes.

The term "vector" refers to an agent (virus or plasmid) used to transmit genetic material to a cell or organism. A vector can be a "cloning vector" used to carry a fragment of DNA into a recipient cell for the purpose of gene cloning, or an "expression vector" used to carry a DNA sequence into a suitable host cell and to direct the synthesis of the protein encoded by the DNA sequence. In the current invention, the most suitable vectors are plasmids, i.e. small circular DNA molecules that replicate independently of the genome of the host cell. However, other vectors like cosmids, viruses and phages may also be used, depending on the host cell used.

The present invention relates in particular to a recombinant vector into which the coding sequence for any of the polypeptides of the invention is operably linked to a control sequence capable of providing the expression of the coding sequence by the specific host.

The expression "operably linked to" refers to a juxtaposition where the components are configured so as to perform their usual function. Thus, regulatory sequences operably linked to a coding sequence are capable of directing the expression and eventually secretion of the coding gene. The term "control sequence" refers to those sequences involved in the expression of a gene to protein i.e. its transcription and/or translation and/or regulation and/or maturation. Control sequences may thus comprise a promoter sequence, including possible promoter regulation sequences, a ribosome binding site, a sequence coding for a secretion signal, etc. Another example may be that the coding sequence of the polypeptides of the invention is operably linked to another, heterologous coding sequence, being part of the vector sequence, and resulting in the expression of a fusion protein. Thus, in its broadest wording, the term "control sequence" may also comprise the coding sequence of a heterologous protein to which the polypeptides of the invention are fused.

According to yet another embodiment, the present invention relates to a host cell transformed by a recombinant vector comprising any of the polynucleic acid sequences of the invention.

Preferably, said host cell is a bacterial host cell, most preferably E. coli, but it may also include eukaryotic cells like yeast, plant, insect or animal cells.

The techniques for carrying out expression of the polypeptides of the invention in E. coli are demonstrated further in the Examples section. The techniques for carrying out expression in any of the other host cells are well known in the art of recombinant expression technology.

According to a subsequent embodiment, the invention provides for a recombinant polypeptide produced by
    growing a culture of a transformed host cell as defined above, under conditions which allow the expression and
    possibly secretion of the encoded polypeptide, and
recovering the expressed polypeptide from the culture.

According to a possible embodiment, said recombinant polypeptide may be a fusion protein, consisting of the polypeptide of the invention fused in frame to a heterologous (poly)peptide. As described above, a fusion protein may bring about possible desired effect to the polypeptides of the invention.

Another embodiment of the invention provides for an antibody, monoclonal or polyclonal, reacting specifically with the polypeptides of the invention.

Preferably, said antibody is different from the monoclonal antibody BATO 214 which has been described earlier by Saavedra et al. (1990).

Antibodies according to this preferred embodiment of the invention include specific polyclonal antisera prepared against the T. gondii polypeptides of the invention, and showing no cross-reactivity to other T. gondii proteins. It also includes monoclonal antibodies prepared against the T. gondii polypeptides of the invention.

The monoclonal antibodies of the invention can be produced by any hybridoma formed according to classical methods known in the art, i.e. by fusion of splenic cells of an animal, particularly of a mouse or rat, infected with T. gondii or immunized against the polypeptides according to the invention defined above on the one hand, and of cells of a myeloma cell line on the other hand, and selected by the ability of the hybridoma to produce monoclonal antibodies recognizing the polypeptides which have been initially used for immunization of the animals.

The monoclonal antibodies according to a preferred embodiment of the invention may be humanized versions of the mouse monoclonal antibodies made by means of recombinant DNA technology, departing from the mouse and/or human genomic DNA sequences coding for H and L chains or from cDNA clones coding for H and L chains.

Also fragments derived from these monoclonal antibodies such as Fab, F(ab)'$_2$ and ssFv ("single chain variable fragment"), providing they have retained the original binding properties, form part of the present invention. Such fragments are commonly generated by, for instance, enzymatic digestion of the antibodies with papain, pepsin, or other proteases. It is well known to the person skilled in the art that monoclonal antibodies, or fragments thereof, can be modified for various uses.

The antibodies involved in the invention can be labelled by an appropriate label of the enzymatic, fluorescent, or radioactive type.

The invention also relates to the use of the proteins of the invention, muteins thereof, or fragments thereof, for the selection of recombinant antibodies by the process of repertoire cloning (Perrson et al., 1991).

According to a preferred embodiment of the present invention, an antibody, or an antigen-binding fragment F(ab')$_2$, Fab, single chain Fv and all types of recombinant antibodies, as defined above are further characterized in that they can inhibit the infection by Toxoplasma gondii of the specific cell type which it infects in vivo.

According to another embodiment, the present invention relates to a monoclonal antibody as defined above, obtainable by a process comprising at least the following steps:
    fusing the splenocytes from mice infected with Toxoplasma gondii together with myeloma cells, and
    selecting the anti-T. gondii hybridomas by means of ELISA and subsequent limiting dilution,
    selecting the hybridomas producing a monoclonal antibody, specifically directed against any of the T. gondii polypeptides of the invention by means of ELISA, and,
    recovering the monoclonal antibodies from ascites fluid or from a culture of the selected hybridomas.

The present invention also relates to a hybridoma producing any of the monoclonal antibodies as defined above.

The present invention further relates to an anti-idiotype antibody raised against any of the antibodies as defined above.

The term "anti-idiotype antibodies" refers to monoclonal antibodies raised against the antigenic determinants of the variable region of monoclonal antibodies themselves raised against the Toxoplasma Tg20 polypeptides. These antigenic determinants of immunoglobulins are known as idiotypes (sets of idiotopes) and can therefore be considered to be the "fingerprint" of an antibody (for review see de Préval, 1978; Fleishmann and Davie, 1984). The methods for production of monoclonal anti-idiotypic antibodies have been described by Gheuens and McFarlin (1982). Monoclonal anti-idiotypic antibodies have the property of forming an immunological complex with the idiotype of the monoclonal antibody against which they were raised. In this respect the monoclonal antibody is often referred to as Ab1, and the anti-idiotypic antibody is referred to as Ab2. These anti-idiotype Ab2s may be used as substitutes for the polypeptides of the invention or as competitors for binding of the polypeptides of the invention to their target.

The present invention further relates to antisense peptides derived from the Toxoplasma polypeptides as defined above.

More particularly, the term "antisense peptide" is reviewed by Blalock (1990) and by Roubos (1990). In this respect, the molecular recognition theory (Blalock, 1990) states that not only the complementary nucleic acid sequences interact but that, in addition, interacting sites in proteins are composed of complementary amino acid sequences (sense ligand with receptor or sense ligand with antisense peptides). Thus, two peptides derived from complementary nucleic acid sequences in the same reading frame will show a total interchange of their hydrophobic and hydrophilic amino acids when the amino terminus of one is aligned with the carboxy terminus of the other. This inverted hydropathic pattern might allow two such peptides to assume complementary conformations responsible for specific interaction.

The antisense peptides can be prepared as described in Ghiso et al. (1990). By means of this technology it is possible to logically construct a peptide having a physiologically relevant interaction with a known peptide by simple nucleotide sequence analysis for complementarity, and synthesize the peptide complementary to the binding site.

The present invention still further relates to a method for in vitro diagnosis of *T. gondii* infection comprising at least the step of contacting a sample possibly containing anti-*T. gondii* antibodies, *T. gondii* antigens and/or *T. gondii* nucleic, with:

a polypeptide or peptide as defined above, under conditions allowing the formation of an immunological complex, or, a probe as defined above, under conditions allowing the formation of a hybridization complex, with said nucleic acids of said sample being possibly amplified prior to hybridization, using a primer as defined above, or, an antibody specifically directed against a polypeptide as defined above, under conditions allowing the formation of an immunological complex, or, an anti-idiotype antibody as defined above, under conditions allowing the formation of an antibody-anti-idiotypic complex, or, an antisense peptide as defined above, under conditions allowing the formation of an antigen-antisense peptide complex, and subsequently detecting the complexes formed.

The term "sample" may refer to any biological sample (tissue or fluid) containing *T. gondii* nucleic acids, antibodies or polypeptides.

In a preferential embodiment, the invention relates to a method for detection of anti-*T. gondii* antibodies and the preferred sample in that case is serum or plasma.

In a more specific embodiment, the invention relates to a method for detecting antibodies to *T. gondii* present in a biological sample, comprising:

contacting the biological sample to be analysed with any of the polypeptide as described above, under conditions allowing the formation of an immunological complex, and detecting the immunological complex formed between said antibodies and said polypeptide.

Conditions allowing the formation of an immunological complex are known to the person skilled in the art.

In a special embodiment, the polypeptides being used in the above-described method for detection of anti-*T. gondii* antibodies, can be replaced by anti-idiotype antibodies as described above, acting as their equivalents.

Conditions allowing the formation of an antibody-anti-idiotypic complex are known in the art.

The invention further relates to a method for detecting the presence of *T. gondii* antigens in a biological sample, comprising:

contacting the biological sample to be analysed with an antibody according to the invention, under conditions allowing the formation of an immunological complex, and detecting the immunological complex formed between said antigens and said antibody.

In a special embodiment, the antibodies being used in the above-described method for detection of *T. gondii* antigens, may be replaced by anti-sense peptides as described above, acting as their equivalents.

Conditions allowing the formation of an antigen-antisense peptide complex are known in the art.

Design of immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

An advantageous embodiment provides for a method for detection of anti-*T. gondii* antibodies in a sample, whereby the (poly)peptides of the invention are immobilized on a solid support, eventually on a membrane strip. Different (poly)peptides of the invention may be immobilized together or next to each other on distinct locations (e.g. in the form of parallel lines). The polypeptides of the invention may also be combined in the same assay with other antigens from *Toxoplasma gondii* or from other organisms.

The invention thus also relates to a solid support onto which the (poly)peptides of the invention, possibly in combination with other (poly)peptides, have been immobilized.

Another embodiment of the invention provides for a method for detecting the presence of *T. gondii* polynucleic acids present in a biological sample, comprising:

possibly extracting the polynucleic acids contained in the sample, amplifying the *T. gondii* polynucleic acids with at least one primer as described above, detecting the amplified nucleic acids, possibly after hybridization with a probe as described above.

Conditions allowing hybridization are known in the art and e.g. exemplified in Maniatis et al. (1982). However, according to the hybridization solution (SSC, SSPE, etc.), the probes used should be hybridized at their appropriate temperature in order to attain sufficient specificity (in some cases differences at the level of one nucleotide mutation are to be discriminated).

Amplification of nucleic acids present in a sample prior to detection in vitro may be accomplished by first extracting the nucleic acids present in the sample according to any of the techniques known in the art. In case of extraction of RNA, generation of cDNA is necessary; otherwise cDNA or genomic DNA is extracted.

The amplification methods are detailed above.

Suitable assay methods for purposes of the present invention to detect hybrids formed between oligonucleotide probes according to the invention and the nucleic acid sequences in a sample may comprise any of the assay formats kown in the art. For example, the detection can be accomplished using a dot blot format, the unlabelled amplified sample being bound to a membrane, the membrane being incubated with at least one labelled probe under suitable hybridization and wash conditions, and the presence of bound probe being monitored. Probes can be labelled with radioisotopes or with labels allowing chromogenic or chemiluminescent detection such as horse-radish peroxidase coupled probes.

An alternative is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of detecting T. gondii nucleic acid sequences contained in a biological sample comprises the steps of contacting amplified fragments of the polynucleic acids of the invention, with a solid support onto which probes as defined above, have been previously immobilized.

In a very specific embodiment, the probes have been immobilized on a membrane strip in the form of parallel lines. This type of reverse hybridization method is specified further as a Line Probe Assay (LiPA).

The invention thus also relates to a solid support onto which the polynucleotides of the invention have been immobilized.

According to another embodiment, the present invention relates to a method using at least one of the polypeptides or peptides of the invention, possibly in combination with other T. gondii polypeptides, for measuring a cellular immune response in an individual which has been in contact with the T. gondii pathogen, said cellular immune response being measured either in vivo, such as a delayed type hypersensitivity reaction upon subcutaneous injection of the polypeptides of the invention, or in vitro, such as stimulation of periferal blood lymphocytes of secretion of interferon-gamma, upon addition of the polypeptides of the invention to a sample of periferal blood lymphocytes under conditions allowing recognition of the polypeptides by the cells responsive for the immune response, conditions which are known to the person skilled in the art.

The present invention also relates to a kit for detecting anti-T. gondii antibodies, or T. gondii nucleic acids or T. gondii antigens according to any of the methods as defined here above, comprising at least one of the T. gondii polypeptides or peptides as defined above, or any of the T. gondii nucleic acids as defined above, more specifically any of the probes or primers as defined above, or any of the antibodies as defined above, or any of the anti-idiotypic antibodies as defined above, or any of the antisense-peptides as defined above.

According to this embodiment, the detection of antibodies against the T. gondii polypeptides of the invention is preferred over the detection of nucleic acids of polypeptides.

The present invention relates more particularly to a kit for determining the presence of anti-T. gondii polypeptide antibodies as defined above (=a serodiagnostic kit/assay) in a biological sample, comprising:
- at least one polypeptide or peptide as defined above, possibly in combination with other polypeptides or peptides from T. gondii, with said polypeptides being preferentially immobilized on a solid substrate,
- a buffer, or components necessary for producing the buffer, enabling a binding reaction between the polypeptides of the invention and the antibodies possibly present in the biological sample,
- means for detecting the immune complexes formed in the preceding binding reaction,
- possibly also including an automated scanning and interpretation device for inferring the presence of T. gondii antibodies in the sample.

The kit or method according to this aspect of the present invention may comprise in addition to peptide or polypeptide antigens according to the invention, also other T. gondii antigenic proteins or peptides known in the art (such as outer membrane protein (OMP) proteins or peptides), or other bacterial antigenic proteins or peptides in general.

The combination of different antigens in one single detection method or kit as described above, may have certain advantages, such as for example:
- achieving a higher test sensitivity: e.g. by combining several antigenic determinants from T. gondii, the number of correctly identified positive sera may be greater, and/or
- enabling differentiation between chronic and acute T. gondii infection.

In a preferential embodiment, the invention relates to a serodiagnostic method and/or kit as described above, whereby the polypeptides and peptides of the invention are combined with the Tg34 antigen of T. gondii, or fragments thereof, as described by van Gelder et al. 1993.

Another particular case of combination, also in included in the current invention, is the combination of the polypeptides of the current invention with antigenic fragments located in the C-terminal part of the Tg20-protein, i.e. sequences located in the region from amino acid position 197 to amino acid position 235 of the sequence represented in FIG. 1b (SEQ ID NO 2). As described further in the examples section, the most immunodominant epitopes of the Tg20 protein reside in the region extending from amino acid position 1 to amino acid position 197, more particularly in the region extending from position 95 to position 145 as represented in FIG. 1b. However, it may be necessary, in certain instances, to combined the polypeptides of the invention with (poly)peptide fragments originating from the less antigenic C-terminal part of Tg20.

Said combination of antigens in one assay may be accomplished in different ways, depending on the application or test format. For example, antigenic fragments of several polypeptides (e.g. Tg20 of the invention and Tg34) may be immobilized together on a solid surface (microtiter plate or membrane . . . ), in the same location or in distinct locations. A preferred example of the latter test format is a Line Immuno Assay (LIA, INNOGENETICS) where different antigenic fragments are immobilized as parallel lines on a membrane strip, thus allowing to monitor the differential reactivities with the different antigenic fragments.

Alternatively, the combination of the polypeptides of the invention with other T. gondii antigenic determinants, may be made on the molecule level, i.e. by the creation of a "superantigen" for the detection of T. gondii infection, combining different antigenic epitopes in one molecule. Said "superantigen" may be produced by recombinant DNA techniques, known in the art, e.g. by linking operably together the different DNA sequences encoding the different antigenic sites and expressing them in a suitable host.

It is to be understood that the above-described combination is not exclusively to be used in serodiagnostic assays, but may also prove to be useful in other types of diagnostic assays, and/or in vaccine compositions.

In a very specific embodiment the invention relates to a kit for the detection of anti-T. gondii antibodies in a biological sample as described above, whereby the polypeptides of the invention are replaced by the anti-idiotype antibodies as described above.

The invention further relates to a diagnostic kit for the detection of antigens of T. gondii present in a biological sample, said kit comprising an antibody as described above, with said antibody being preferably bound to a solid support.

In a very specific embodiment, the invention relates to a diagnostic kit for the detection of antigens of T. gondii present in a biological sample, whereby the antibody as described above is replaced by an antisense peptide.

The invention further also relates to a diagnostic kit for the detection of *T. gondii* polynucleic acids present in a sample, said kit comprising a probe as described above and/or a primer as described above.

According to a preferred embodiment, the present invention relates to a kit or method for diagnosis of *T. gondii* infection as defined above, further characterized in that said polypeptides, peptides, polynucleic acids, antibodies, anti-idiotypic antibodies or anti-sense peptides are particularly useful for differentiating in vitro *T. gondii* chronically infected individuals from acutely infected individuals.

According to another embodiment, the present invention relates to a vaccine composition which provides protective immunity against *T. gondii* infection comprising as an active principle one or more of the *T. gondii* polypeptides according to the invention, or one or more of the polynucleic acid sequences or recombinant vectors according to the invention, said active principle being combined with a pharmaceutically acceptable carrier.

According to a special embodiment, the vaccine composition as described above may comprise as an active principle one of the anti-idiotype antibodies as described above.

Besides the *T. gondii* proteins according to the invention, said vaccine composition may also comprise any other Toxoplasma immunogenic components (such as Rop2 (Tg34), Gra1, Gra2, Sag1, Sag2 antigens e.o.) or any other bacterial or other immunogenic components in general.

In a specific embodiment, polynucleic acid sequences coding for any of the polypeptides as defined above, are used as a vaccine, either as naked DNA or as part of recombinant vectors. In this case, it is the aim that said nucleic acids which are administered to the individual to be immunized, are expressed into immunogenic protein/peptide in situ and thus confer protection to the vaccinated host (e.g. Ulmer et al., 1993).

The active ingredients of such a vaccine composition may be administered orally, subcutaneously, conjunctivally, intramuscularly, intranasally, or via any other route known in the art including for instance via the binding to carriers, via incorporation into liposomes, by adding adjuvants known in the art, etc.

The invention also relates to any of the above-mentioned substances (polypeptides, antibodies, polynucleic acids, anti-idiotype antibodies, antisense peptides) for use as a medicament, more particularly for any of the medical (diagnostic or polphylactic) applications as mentioned above.

Furthermore, the invention relates to the use of any of the above-mentioned substances (polypeptides, antibodies, polynucleic acids, anti-idiotype antibodies, antisense peptides) for the manufacture of a medicament, more particularly for the preparation af a vaccine or for the preparation of a diagnostic composition.

FIGURE LEGENDS

FIG. 1

1A Restriction map of the 1260 bp EcoRI fragment of clone Tg20 and position of the different deletion clones analyzed for immune reactivity.

1B–1D Complete nucleic acid (SEQ ID NO 1) and amino acid (SEQ ID NO 2) sequence of the 1260 bp EcoRI fragment of clone Tg20. Relevant restriction sites are indicated.

Arrows indicate possible signal peptide cleavage sites.

Figure 2:
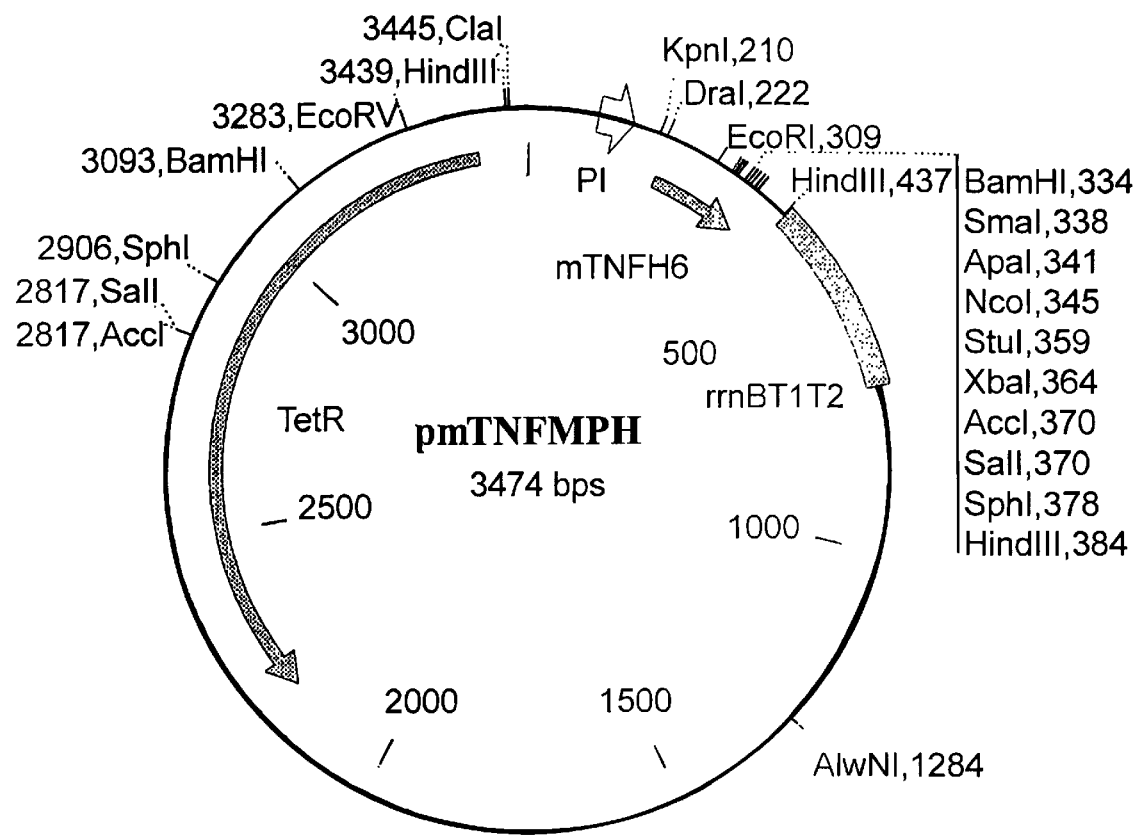

FIG. 2 Map of vector pm TNF.MPH

Figure 3:
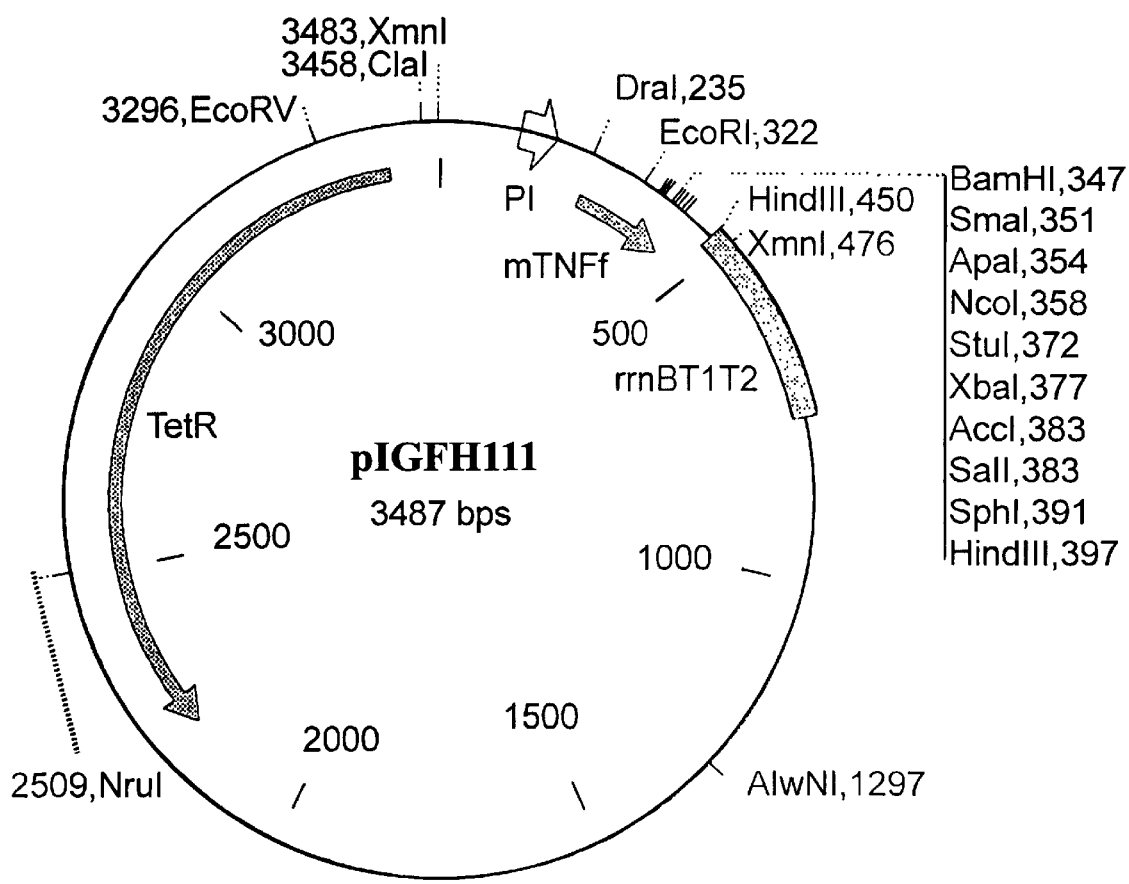

FIG. 3 Map of vector pIGFH111

FIG. 4 Amino acid sequence of mTNF.H6.Tg20 fusion protein. Normal characters represent the amino acid sequence originating from the vector. Bold characters correspond to the Tg20 antigen sequence.

Figure 5:
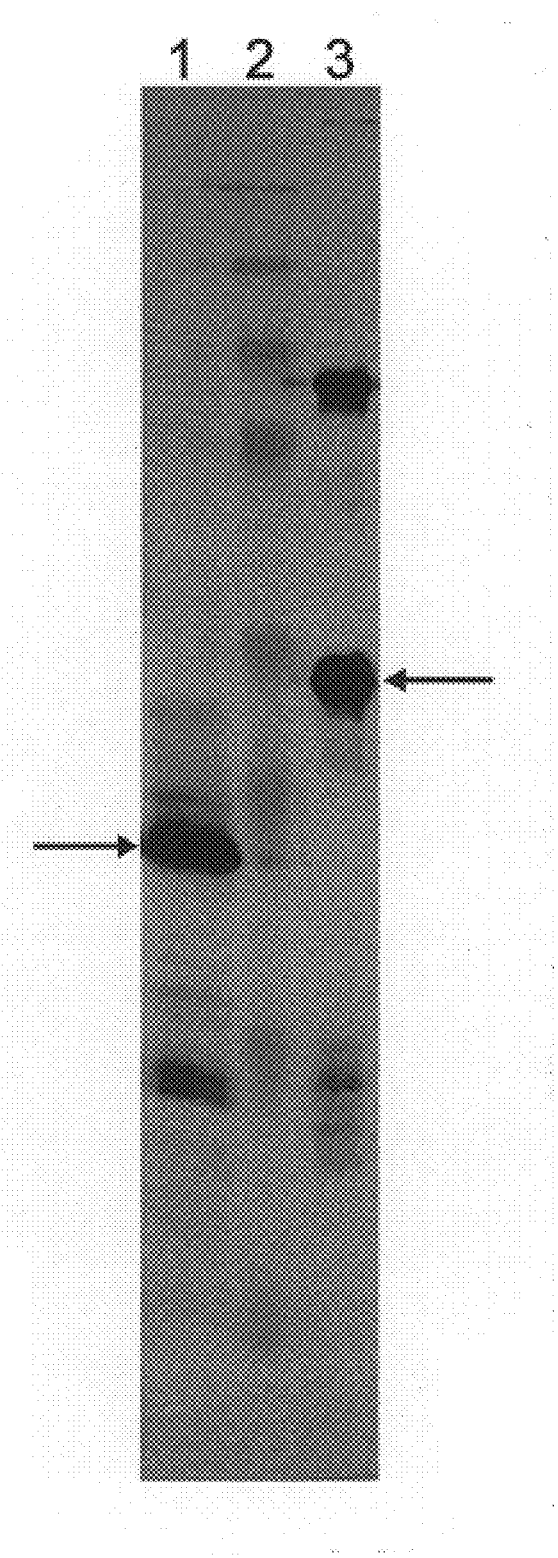

FIG. 5 Reactivity in Western Blot with Mab BATO 214 of the recombinant Tg20 antigen and is naturally occurring counterpart.

Lane 1: *T. gondii* lysate

Lane 2: MW markers (Biolabs) with increasing sizes of 6.5, 16.5, 25.0, 32.5, 47.5, 62.0, 83.0, 175.0 kDa.

Lane 3: purified recombinant Tg20 fusion protein.

FIG. 6 Hydrophylicity plot of the Tg20 antigen (SEQ ID NO 2).

TABLE LEGENDS

Table 1: Amino acid substitutions which may form the basis for the muteins (equivalents) according to the present invention.

Table 2: Reactivity (OD450 values×1000) of different (human) sera in the classical tests used for Toxoplasmosis diagnosis (IF (IgG and IgM) and Biomérieux ELISA test), and in ELISA using Tg20 antigen of the invention, or a fragment thereof (Tg20BN), in ELISA using the Tg34AR antigen, or combinations of the foregoing antigens.

Sera positive in classical testing are numbered from 1 to 95.

Sera negative in classical testing are numbered from 206 to 250.

Table 3: Comparison of reactivity of some of the sera from table 2 with the full size Tg20 antigen and the Tg20 fragment.

TABLE 1

| Amino acids | Synonymous groups |
|---|---|
| Ser (S) | Ser, Thr, Gly, Asn |
| Arg (R) | Arg, His, Lys, Glu, Gln |
| Leu (L) | Leu, Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Leu, Phe, Val, Tyr |
| Phe (F) | Phe, Met, Tyr, Ile, Leu, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Glu, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Glu, Gln |
| Glu (E) | Glu, Gln, Asp, Lys, Asn, His, Arg |
| Met (M) | Met, Ile, Leu, Phe, Val |

TABLE 2

| Serum Nr | IF IgG titre | IF IgM titre | BioMer IgG | Tg34AR | Tg20 | Tg34AR Tg20 | Tg34AR Tg20BN |
|---|---|---|---|---|---|---|---|
| 1 | 1/256 | 1/50 | 1219 | 378 | 524 | 849 | 795 |
| 2 | 1/64 | <1/50 | 616 | 702 | 518 | 1105 | 1101 |
| 3 | 1/64 | <1/50 | 1085 | 197 | 147 | 286 | 251 |
| 4 | 1/64 | <1/50 | 337 | 23 | 33 | 107 | 73 |
| 5 | 1/256 | 1/50 | 716 | 430 | 119 | 586 | 674 |
| 6 | 1/64 | <1/50 | 598 | 874 | 99 | 664 | 845 |
| 7 | 1/64 | <1/50 | 988 | 487 | 103 | 653 | 871 |
| 8 | 1/64 | <1/50 | 660 | 183 | 54 | 433 | 381 |
| 9 | 1/1024 | <1/50 | 809 | 1473 | 429 | 1608 | 1821 |
| 10 | 1/256 | <1/50 | 952 | 507 | 257 | 685 | 712 |
| 11 | 1/256 | <1/50 | 1014 | 201 | 117 | 252 | 301 |
| 12 | 1/64 | <1/50 | 1014 | 678 | 344 | 1048 | 1074 |
| 13 | 1/256 | <1/50 | 1102 | 313 | 375 | 474 | 603 |
| 14 | 1/64 | | 876 | 652 | 1010 | 1443 | 1304 |
| 15 | 1/256 | | 1093 | 260 | 983 | 1049 | 564 |
| 16 | 1/64 | | 956 | 213 | 183 | 435 | 439 |
| 17 | 1/64 | <1/50 | 262 | 85 | 136 | 195 | 192 |
| 18 | 1/1024 | <1/50 | 1153 | 1058 | 1413 | 1904 | 1856 |
| 19 | 1/64 | <1/50 | 510 | 142 | 8 | 533 | 401 |
| 20 | 1/256 | <1/50 | 1381 | 678 | 669 | 943 | 1124 |
| 21 | 1/64 | <1/50 | 768 | 108 | 249 | 493 | 340 |
| 22 | 1/1024 | 1/50 | 1361 | 692 | 748 | 1401 | 1196 |
| 23 | 1/256 | <1/50 | 1434 | 861 | 374 | 1079 | 1152 |
| 24 | 1/1024 | <1/50 | 1262 | 506 | 283 | 812 | 916 |
| 25 | 1/1024 | 1/100 | 1295 | 1848 | 723 | 2030 | 2096 |
| 26 | 1/256 | <1/50 | 1137 | 303 | 357 | 849 | 593 |
| 27 | 1/1024 | | 1495 | 526 | 649 | 1344 | 1087 |
| 28 | 1/1024 | <1/50 | 1593 | 882 | 2346 | 2105 | 1925 |
| 29 | 1/256 | | 1415 | 274 | 1430 | 1377 | 1199 |
| 30 | 1/1024 | <1/50 | 1391 | 593 | 1248 | 1305 | 1089 |
| 31 | 1/256 | | 1221 | 283 | 1589 | 1527 | 1328 |
| 32 | 1/64 | <1/50 | 173 | 34 | 127 | 213 | 137 |
| 33 | 1/256 | <1/50 | 530 | 42 | 58 | 137 | 141 |
| 34 | 1/256 | <1/50 | 498 | 29 | 342 | 406 | 303 |
| 35 | 1/256 | <1/50 | 1273 | 444 | 336 | 921 | 578 |
| 36 | 1/256 | <1/50 | 873 | 298 | 200 | 384 | 435 |
| 37 | 1/256 | <1/50 | 1074 | 748 | 430 | 1193 | 1205 |
| 38 | 1/256 | | 1351 | 475 | 1154 | 1397 | 1106 |
| 39 | 1/64 | <1/50 | 157 | 31 | 48 | 67 | 62 |
| 40 | 1/64 | <1/50 | 591 | 1360 | 1410 | 869 | 426 |
| 41 | 1/64 | <1/50 | 663 | 175 | 176 | 325 | 378 |
| 42 | 1/256 | <1/50 | 1388 | 595 | 1640 | 1711 | 1624 |
| 43 | 1/64 | <1/50 | 697 | 139 | 127 | 369 | 279 |
| 44 | 1/256 | 1/200 | 1323 | 293 | 1226 | 1442 | 1199 |
| 45 | 1/64 | <1/50 | 237 | 42 | 32 | 49 | 37 |
| 46 | 1/256 | <1/50 | 789 | 226 | 39 | 426 | 472 |
| 47 | 1/64 | | 387 | 115 | 442 | 504 | 547 |
| 48 | 1/1024 | <1/50 | 1224 | 1244 | 1115 | 1765 | 1940 |
| 49 | 1/1024 | <1/50 | 648 | 268 | 366 | 563 | 448 |
| 50 | 1/256 | <1/50 | 646 | 256 | 492 | 697 | 611 |
| 51 | 1/1024 | <1/50 | 1351 | 348 | 845 | 1102 | 636 |
| 52 | 1/256 | <1/50 | 589 | 489 | 280 | 480 | 492 |
| 53 | 1/256 | <1/50 | 355 | 25 | 75 | 118 | 98 |
| 54 | 1/1024 | <1/50 | 1186 | 1727 | 1199 | 1874 | 1891 |
| 55 | 1/256 | <1/50 | 1180 | 736 | 1840 | 1836 | 1723 |
| 56 | 1/1024 | 1/50 | 1367 | 1542 | 2515 | 2114 | 1929 |
| 57 | 1/256 | 1/50 | 569 | 164 | 1221 | 972 | 400 |
| 58 | 1/1024 | | 832 | 356 | 421 | 585 | 486 |
| 59 | 1/256 | <1/50 | 959 | 270 | 909 | 778 | 431 |
| 60 | 1/1024 | 1/100 | 1498 | 1900 | 2669 | 2216 | 2307 |
| 61 | 1/256 | <1/50 | 1041 | 239 | 160 | 514 | 396 |
| 62 | 1/256 | <1/50 | 324 | 64 | 34 | 68 | 48 |
| 63 | 1/64 | <1/50 | 170 | 96 | 64 | 68 | 53 |
| 64 | 1/256 | | 902 | 192 | 901 | 767 | 334 |
| 65 | 1/256 | <1/50 | 1428 | 776 | 1189 | 1609 | 1455 |
| 66 | 1/1024 | <1/50 | 1495 | 1216 | 1559 | 1764 | 1856 |
| 67 | 1/256 | <1/50 | 1042 | 1115 | 364 | 1154 | 1222 |
| 68 | 1/64 | <1/50 | 489 | 91 | 50 | 139 | 127 |
| 69 | 1/64 | <1/50 | 1134 | 1015 | 1493 | 1815 | 1817 |
| 70 | 1/256 | <1/50 | 1247 | 322 | 721 | 1280 | 1004 |
| 71 | 1/1024 | <1/50 | 1352 | 1170 | 529 | 1300 | 1382 |
| 72 | 1/256 | <1/50 | 666 | 423 | 393 | 808 | 753 |
| 73 | 1/64 | <1/50 | 673 | 176 | 36 | 110 | 141 |
| 74 | 1/256 | | 613 | 457 | 712 | 962 | 627 |
| 75 | 1/1024 | | 1001 | 1290 | 302 | 1687 | 1720 |
| 76 | 1/64 | <1/50 | 258 | 8 | 12 | 33 | 19 |

TABLE 2-continued

| Serum Nr | IF IgG titre | IF IgM titre | BioMer IgG | Tg34AR | Tg20 | Tg34AR Tg20 | Tg34AR Tg20BN |
|---|---|---|---|---|---|---|---|
| 77 | 1/256 | 1/100 | 1224 | 330 | 972 | 1197 | 909 |
| 78 | 1/256 | <1/50 | 1167 | 665 | 271 | 974 | 891 |
| 79 | 1/64 | <1/50 | 462 | 37 | 57 | 121 | 109 |
| 80 | 1/256 | <1/50 | 1419 | 677 | 1067 | 1338 | 1165 |
| 81 | 1/256 | 1/50 | 1151 | 284 | 377 | 642 | 569 |
| 82 | 1/256 | <1/50 | 734 | 224 | 24 | 22 | 10 |
| 83 | 1/64 | <1/50 | 617 | 108 | 204 | 344 | 145 |
| 84 | 1/64 | <1/50 | 134 | 61 | 66 | 96 | 62 |
| 85 | 1/256 | <1/50 | 1203 | 1546 | 21 | 821 | 1377 |
| 86 | 1/64 | <1/50 | 239 | 95 | 243 | 383 | 356 |
| 87 | 1/64 | <1/50 | 419 | 56 | 310 | 410 | 295 |
| 88 | 1/256 | <1/50 | 1288 | 783 | 370 | 992 | 888 |
| 89 | 1/256 | <1/50 | 1188 | 428 | 316 | 599 | 573 |
| 90 | 1/256 | <1/50 | 350 | 82 | 102 | 198 | 123 |
| 91 | 1/1024 | <1/50 | 1451 | 279 | 1051 | 1186 | 910 |
| 92 | 1/256 | <1/50 | 1151 | 536 | 424 | 819 | 854 |
| 93 | 1/256 | <1/50 | 1198 | 470 | 215 | 861 | 644 |
| 94 | 1/256 | <1/50 | 911 | 532 | 523 | 729 | 593 |
| 95 | 1/256 | <1/50 | 770 | 432 | 211 | 420 | 406 |
| 206 | <1/64 | <1/50 | 19 | 1 | 10 | 10 | 7 |
| 207 | <1/64 | <1/50 | 30 | 3 | 10 | 17 | 7 |
| 208 | <1/64 | <1/50 | 37 | 53 | 18 | 18 | 10 |
| 209 | <1/64 | <1/50 | 52 | 0 | 59 | 80 | 36 |
| 210 | <1/64 | <1/50 | 31 | 0 | 13 | 16 | 8 |
| 211 | <1/64 | <1/50 | 12 | 50 | 19 | 20 | 11 |
| 212 | <1/64 | <1/50 | 17 | 11 | 14 | 15 | 10 |
| 213 | <1/64 | <1/50 | 14 | 5 | 12 | 13 | 10 |
| 214 | <1/64 | <1/50 | 24 | 18 | 19 | 15 | 10 |
| 215 | <1/64 | <1/50 | 14 | 0 | 12 | 13 | 8 |
| 216 | <1/64 | <1/50 | 25 | 34 | 37 | 26 | 18 |
| 217 | <1/64 | <1/50 | 40 | 14 | 20 | 17 | 12 |
| 218 | <1/64 | <1/50 | 37 | 3 | 12 | 12 | 10 |
| 219 | <1/64 | <1/50 | 12 | 25 | 142 | 86 | 35 |
| 220 | <1/64 | <1/50 | 15 | 4 | 19 | 19 | 12 |
| 222 | <1/64 | <1/50 | 22 | 122 | 11 | 11 | 5 |
| 223 | <1/64 | <1/50 | 43 | 12 | 10 | 10 | 7 |
| 224 | <1/64 | <1/50 | 39 | 5 | 25 | 25 | 14 |
| 225 | <1/64 | <1/50 | 61 | 15 | 59 | 24 | 8 |
| 226 | <1/64 | <1/50 | 26 | 12 | 37 | 24 | 7 |
| 227 | <1/64 | <1/50 | 30 | 4 | 15 | 12 | 8 |
| 228 | <1/64 | <1/50 | 35 | 257 | 16 | 66 | 100 |
| 229 | <1/64 | <1/50 | 28 | 6 | 36 | 39 | 9 |
| 230 | <1/64 | <1/50 | 31 | 5 | 11 | 10 | 6 |
| 231 | <1/64 | <1/50 | 27 | 3 | 9 | 12 | 7 |
| 232 | <1/64 | <1/50 | 29 | 5 | 36 | 35 | 21 |
| 234 | <1/64 | <1/50 | 38 | 4 | 24 | 17 | 10 |
| 235 | <1/64 | <1/50 | 30 | 9 | 21 | 38 | 11 |
| 236 | <1/64 | <1/50 | 33 | 16 | 16 | 20 | 15 |
| 237 | <1/64 | <1/50 | 45 | 27 | 59 | 38 | 9 |
| 238 | <1/64 | <1/50 | 29 | 2 | 23 | 26 | 5 |
| 239 | <1/64 | <1/50 | 24 | 0 | 32 | 51 | 116 |
| 240 | <1/64 | <1/50 | 38 | 5 | 13 | 11 | 8 |
| 241 | <1/64 | <1/50 | 30 | 5 | 17 | 10 | 11 |
| 242 | <1/64 | <1/50 | 29 | 15 | 15 | 30 | 7 |
| 243 | <1/64 | <1/50 | 23 | 1 | 12 | 16 | 8 |
| 244 | <1/64 | <1/50 | 34 | 2 | 136 | 125 | 11 |
| 245 | <1/64 | <1/50 | 25 | 1 | 12 | 16 | 7 |
| 246 | <1/64 | <1/50 | 27 | 35 | 19 | 13 | 6 |
| 247 | <1/64 | <1/50 | 27 | 0 | 12 | 12 | 8 |
| 248 | <1/64 | <1/50 | 25 | 1 | 13 | 13 | 8 |
| 249 | <1/64 | <1/50 | 26 | 2 | 45 | 15 | 9 |
| 250 | <1/64 | <1/50 | 29 | 5 | 30 | 21 | 10 |

TABLE 3

| Serum Nr | IF IgG titre | IF IgM titre | BioMer IgG | Tg20 | Tg20BN |
|---|---|---|---|---|---|
| 1 | 1/256 | 1/50 | 1219 | 714 | 703 |
| 2 | 1/64 | <1/50 | 616 | 746 | 607 |
| 3 | 1/64 | <1/50 | 1085 | 203 | 130 |
| 4 | 1/64 | <1/50 | 337 | 71 | 42 |
| 5 | 1/256 | 1/50 | 716 | 225 | 124 |
| 6 | 1/64 | <1/50 | 598 | 175 | 91 |
| 7 | 1/64 | <1/50 | 988 | 209 | 137 |
| 8 | 1/64 | <1/50 | 660 | 95 | 59 |

TABLE 3-continued

| Serum Nr | IF IgG titre | IF IgM titre | BioMer IgG | Tg20 | Tg20BN |
|---|---|---|---|---|---|
| 9 | 1/1024 | <1/50 | 809 | 570 | 297 |
| 10 | 1/256 | <1/50 | 952 | 380 | 196 |
| 11 | 1/256 | <1/50 | 1014 | 146 | 173 |
| 12 | 1/64 | <1/50 | 1014 | 529 | 393 |
| 13 | 1/256 | <1/50 | 1102 | 374 | 253 |
| 14 | 1/64 | | 876 | 1416 | 1108 |
| 15 | 1/256 | | 1093 | 1194 | 350 |
| 16 | 1/64 | | 956 | 286 | 160 |
| 17 | 1/64 | <1/50 | 262 | 235 | 159 |
| 18 | 1/1024 | <1/50 | 1153 | 1776 | 1050 |
| 19 | 1/64 | <1/50 | 510 | 510 | 278 |
| 20 | 1/256 | <1/50 | 1381 | 268 | 185 |
| 21 | 1/64 | <1/50 | 768 | 335 | 141 |
| 22 | 1/1024 | 1/50 | 1361 | 985 | 639 |
| 23 | 1/256 | <1/50 | 1434 | 532 | 309 |
| 24 | 1/1024 | <1/50 | 1262 | 435 | 278 |
| 25 | 1/1024 | 1/100 | 1295 | 974 | 594 |
| 26 | 1/256 | <1/50 | 1137 | 369 | 328 |
| 27 | 1/1024 | | 1495 | 736 | 553 |
| 28 | 1/1024 | <1/50 | 1593 | 2449 | 2270 |
| 29 | 1/256 | | 1415 | 1612 | 1320 |
| 30 | 1/1024 | <1/50 | 1391 | 1242 | 1013 |
| 31 | 1/256 | | 1221 | 1476 | 1612 |
| 32 | 1/64 | <1/50 | 173 | 168 | 166 |
| 33 | 1/256 | <1/50 | 530 | 148 | 86 |
| 34 | 1/256 | <1/50 | 498 | 324 | 379 |
| 35 | 1/256 | <1/50 | 1273 | 578 | 75 |
| 36 | 1/256 | <1/50 | 873 | 242 | 244 |
| 37 | 1/256 | <1/50 | 1074 | 490 | 447 |
| 38 | 1/256 | | 1361 | 1268 | 900 |
| 30 | 1/64 | <1/50 | 157 | 91 | 45 |
| 40 | 1/64 | <1/50 | 591 | 1128 | 84 |
| 41 | 1/64 | <1/50 | 663 | 167 | 161 |
| 42 | 1/256 | <1/50 | 1388 | 1701 | 1538 |
| 43 | 1/64 | <1/50 | 697 | 195 | 80 |
| 44 | 1/256 | 1/200 | 1323 | 1620 | 1239 |
| 45 | 1/64 | <1/50 | 237 | 54 | 70 |
| 46 | 1/256 | <1/50 | 789 | 68 | 49 |
| 47 | 1/64 | | 387 | 623 | 534 |
| 48 | 1/1024 | <1/50 | 1224 | 1448 | 844 |
| 49 | 1/1024 | <1/50 | 648 | 390 | 290 |
| 50 | 1/256 | <1/50 | 646 | 712 | 470 |
| 206 | <1/64 | <1/50 | 19 | 18 | 13 |
| 207 | <1/64 | <1/50 | 30 | 17 | 10 |
| 208 | <1/64 | <1/50 | 37 | 31 | 22 |
| 209 | <1/64 | <1/50 | 52 | | |
| 210 | <1/64 | <1/50 | 31 | 24 | 14 |
| 211 | <1/64 | <1/50 | 12 | 31 | 15 |
| 212 | <1/64 | <1/50 | 17 | 36 | 27 |
| 213 | <1/64 | <1/50 | 14 | 21 | 15 |
| 214 | <1/64 | <1/50 | 24 | 57 | 13 |
| 215 | <1/64 | <1/50 | 14 | 19 | 10 |
| 216 | <1/64 | <1/50 | 25 | 20 | 15 |
| 217 | <1/64 | <1/50 | 40 | 43 | 20 |
| 218 | <1/64 | <1/50 | 37 | 15 | 10 |
| 219 | <1/64 | <1/50 | 12 | 163 | 143 |
| 220 | <1/64 | <1/50 | 15 | 39 | 28 |
| 222 | <1/64 | <1/50 | 22 | 17 | 10 |
| 223 | <1/64 | <1/50 | 43 | 29 | 14 |
| 224 | <1/64 | <1/50 | 39 | 71 | 80 |
| 225 | <1/64 | <1/50 | 61 | 73 | 82 |
| 226 | <1/64 | <1/50 | 26 | 37 | 22 |
| 227 | <1/64 | <1/50 | 30 | 22 | 10 |
| 229 | <1/64 | <1/50 | 28 | 32 | 13 |
| 230 | <1/64 | <1/50 | 31 | 16 | 9 |
| 231 | <1/64 | <1/50 | 27 | 12 | 10 |
| 232 | <1/64 | <1/50 | 29 | 53 | 96 |
| 234 | <1/64 | <1/50 | 38 | 54 | 71 |
| 235 | <1/64 | <1/50 | 30 | 46 | 64 |
| 236 | <1/64 | <1/50 | 33 | 29 | 15 |
| 237 | <1/64 | <1/50 | 45 | 60 | 59 |
| 238 | <1/64 | <1/50 | 29 | 37 | 18 |
| 239 | <1/64 | <1/50 | 24 | 67 | 95 |
| 240 | <1/64 | <1/50 | 38 | 23 | 12 |
| 241 | <1/64 | <1/50 | 30 | 32 | 36 |
| 242 | <1/64 | <1/50 | 29 | 24 | 13 |
| 243 | <1/64 | <1/50 | 23 | 21 | 22 |
| 244 | <1/64 | <1/50 | 34 | 117 | 22 |
| 245 | <1/64 | <1/50 | 25 | 18 | 15 |

EXAMPLES

Example 1: Materials and Methods

Reagents.

All reagents were of analytical grade and obtained from Merck (Darmstadt, Germany), Sigma (St. Louis, Mo.) or Bio-Rad Laboratories (Richmond, Calif.). Restriction enzymes and DNA modifying enzymes were purchased from Boehringer Mannheim (Brussels, Belgium) and were used according to the manufacturer's instructions. Protein concentrations were determined by the bicinchoninic acid method (Pierce, Rockford, Ill.)

Monoclonal antibodies.

Monoclonal antibody BATO 214 was prepared as described in Saavedra et al., (1990). Anti-TNF monoclonal was produced from hybridoma culture supernatant.

Human sera.

The serum samples used in this study were referred to the clinical biology laboratory for routine screening or diagnosis of toxoplasmosis. These samples were tested with immuno fluorescence (IF) for IgG and IgM (BioMérieux, Brussels). The positive sera were given numbers from 1 to 95 and the negative sera from 206 to 250. Those sera were tested again with the Toxo-IgG Micro ELA (ELISA) of BioMérieux. Two negative sera showing discrepant results with the IFA test were eliminated from the panel. The reactivities obtained with the panel of sera in the classical reference tests of Biomérieux are represented in table 2.

Parasites and lysate.

RH and Wiktor strains of Toxoplasma gondii were grown as described by Saavedra et al (1991).

Construction of c-DNA library in $\lambda$.gt11, screening and lysogen preparation.

Described in Saavedra et al (1991).

Gel electrophoresis and western blotting. The total E. coli extracts or Toxoplasma lysate were analyzed by SDS-PAGE (12.5%) in the presence of $\beta$-mercaptoethanol as described by Laemmli (1970). Eventually, proteins were transferred to nitrocellulose membranes by the wet western blotting technique (Towbin et al., 1979) in carbonate buffer (10 mM $NaHCO_3$, 3 mM $Na_2CO_3$, 20% (v/v) methanol). The membrane was saturated with 5% fat free milk in TNT (10 mM Tris, 150 mMNaCl, O,O5% (v/v)Tween20) for 1 h, followed by two washes in TNT. The membranes were incubated with monoclonals or sera appropriately diluted in TNT containing 1% BSA for 90 min. Before use, sera were preabsorbed on ice for 30 min using 10% E. coli lysate in the dilution buffer (TNT+1% BSA). After three washes with TNT, the bands were revealed with rabbit anti-mouse IgG conjugate (Dako, Denmark) or rabbit anti-human IgG conjugate (Dako, Denmark) AP labelled. Conjugates were diluted 1/2000. The AP activity was revealed by using the chromogenic substrate nitroblue tetrazolium-5-bromo-4-chloro-3-indolyl-phosphate in 50 mM trisHCl (pH 9.5), 150 mM NaCl, 5 mM $MgCl_2$ buffer (Blake et al. 1984).

ELISA with recombinant antigens. ELISA plates (Immuno Plate Maxisorp F96; Nunc, Roskilde, Denmark)

were coated by incubation at 37° C. for 1 h. with a recombinant antigen solution (100 μl/well) in carbonate buffer 0.1 M pH 9.5 for antigen Tg20 (2 μg/ml) or in glycine-HCL 0.2 M pH 4 for antigen Tg34AR (6 μ/ml). Blocking of the solid phase was carried out by incubation for 1 h at 37° with phosphate buffered saline (PBS) containing 0.1% casein (300 μl/well). After three washes with PBS containing 0.05% Tween 20 (washing buffer), human sera were added at a 1/100 dilution in sample diluent (PBS+0.1% casein+0.01% Triton X-705+1% E. coli lysate (v/V)). Incubation was done for 1.5 h at 37°. The wells were then washed four times and incubated with horseradish peroxidase-labelled goat anti-human IgG (Fc-fragment) Bethesda Research Laboratories, Gaitersburg, Md.) at a 1/5000 dilution in PBS+0.1% casein, for 1 h at 37°. After four washes, the peroxidase activity was detected with $H_2O_2$ and 3.3',5,5'-tetramethyl-benzidine. The reaction was stopped after 30 min by adding 100 μl of 1 N $H_2SO_4$ and the O.D. was read at 450 nm.

Example 2: Identification and Sequencing of Clone Tg20

Antigen Tg34AR, a C-terminal fragment of Tg34 (=ROP2), detects 89% of Toxoplasma positive sera in ELISA as described by Van Gelder et al. 1993. Antigen Tg34AR has been retested with the serum samples, described in Example 1, resulting in a test sensitivity of 77% (cut off value=mean of O.D. of negative sera+3 standard deviations (sd), serum dilution 1/100).

Sera that were missed out by the Tg34AR ELISA, or that were only borderline positive, were used to screen a number of lambda gt11 lysogens which had previously been described to be moderately reactive with a pool of human and/or murine anti-T. gondii antibodies in WB (Saavedra et al.(1991)). This strategy leads to the identification of clones which express an antigen "complementary" to Tg34AR, i.e. which reacts with most of the sera which cannot be detected by the Tg34AR antigen.

The following λgt11 clones, belonging to different hybridisation groups, were chosen for screening: Tg6, Tg13, Tg18, Tg19, Tg20, Tg27, Tg34 and Tg46. The lysogens of the clones were induced, producing β- galactosidase fusion proteins, and subsequently analyzed on Western Blot with the above-selected sera.

Clones Tg13, Tg19 and Tg27 were probed with only three sera (#4, 21, 33). They showed only a very weak reactivity and were therefore not analysed further.

Clones Tg6, Tg18, Tg20, Tg46, Tg47 and Tg34 were probed with sera #4, 21, 33, 17, 39, 53, 68, 45, 63, 79, 83 and 87. Serum #18 was used as a positive control (high titre in ELISA Tg34AR). Clone Tg34 is the previously characterised clone (=Rop2), of which Tg34AR is a fragment.

Clone Tg47 produced β galactosidase only, and was used as a negative control.

Clone Tg20 reacted with 10/13 sera, clone Tg6 reacted with 8/13 sera, clone Tg46 reacted with 3/13 sera. Sera #17, #45 and #63 did not react with any of the clones. From these results, clone Tg20 was chosen for further characterization and sequencing.

The EcoRI fragment of 1260 bp contained in clone Tg20 was transferred from λgt11 to pBluescript KS+, for restriction analysis and sequencing. To facilitate sequencing, one subclone containing the 5' EcoRI-HindIII fragment of 399 bp was ligated into pBluescript KS+ as well. Primers were designed to elucidate the complete sequence of the clone. Every part of the sequence was at least sequenced on both strands. The sequence of the full EcoRI-insert (1260 bp) is shown in FIG. 1 (SEQ ID NO 1). An open reading frame of 705 bp (1–705) was identified, coding for a protein with a theoretical calculated molecular weight of 25,695 kDa, the sequence of which is represented in FIG. 1 (SEQ ID NO 2).

Example 3: Expression in E. coli of Recombinant Tg20 Antigen

1. Construction of recombinant vector

The 1260 bp by EcoRI-fragment of clone Tg20 was transferred to vector pmTNFMPH (Innogenetics) for expression. This vector (see FIG. 2) enables expression of recombinant proteins in E. coli as fusion proteins with a short mouse tumor necrosis factor (mTNF) peptide. Moreover, the vector also confers a polyhistidine sequence of six consecutive histidine residues to the fusion protein, allowing fast and efficient purification using immobilized metal affinity chromatography (IMAC).

The vector pmTNFMPH was digested with ApaI and blunted with T4 DNA polymerase. The Tg20 1260 bp-fragment was recovered from pBluescriptKS+Tg20 by EcoRI digestion and blunting with T4 DNA polymerase. Ligation of both fragments with T4 DNA ligase confers an in frame fusion between the ORF of Tg20 and the mTNF-his6 leader peptide.

This fusion protein contains 37 aa provided by the leader peptide and 235 aa encoded by the Toxoplasma gene fragment. The amino acid sequence of the fusion protein is shown in FIG. 4 (SEQ ID NO 8).

2. E. coli expression of recombinant Tg20 antigen

The transcription of heterologous genes cloned in the expression vector pmTNFMPH is initiated y the early leftward lambda promoter (P1) which is controlled by the C1 repressor. The host cell for expression is E. coli strain MC1061 [pAC1], containing a compatible plasmid which carries the C1-857 mutant gene, encoding a temperature sensitive variant of the C1 repressor. This allows the initiation of expression of heterologous genes by shifting the temperature from 28° C. to 42° C.

Cells of strain MC1061 [pAC1] were transformed with the expression plasmid pmTNFMPH-Tg20 and grown at 28° C. An overnight culture was used to inoculate (1/100) 25 ml LB medium containing tetracyclin (10 μg/ml), which, was further grown at 28° C. (275 rpm) until the O.D. (at 600 nm) reached 0.2. The culture was divided into two equal parts, one of which was shifted to 42° C., while the second part was kept at 28° C.

At 1.5 h intervals, samples were taken and analysed on SDS-PAGE and western blotting using anti-mTNF monoclonal antibodies. The fusion protein mTNFTg20 was detectable on Coomassie Blue stained gels at a MW of approximately 29 kDa Western blots confirmed the identity of this band, which was only present in the induced cultures. From these experiments the conditions for a large scale fermentation of the strain were determined (see example 4).

3. Characterization of the Tg20 antigen: reaction with monoclonal antibodies and MW of the corresponding natural T. gondii antigen Total lysate of cells expressing mTNF.H6Tg20 (shortly recombinant Tg20) was run on a polyacrylamide (PA) gel and transferred to a nitrocellulose membrane. A set of monoclonal antibodies reacting with T. gondii proteins with small molecular weight, as described by Saavedra et al (1990), were probed against with WB. Only monoclonal antibody BATO 214 reacted with this antigen at a MW of about 29 kDa.

On a 12.5% PA gel total toxoplasma lysate and purified recombinant Tg20 were run in parallel and transferred to nitrocellulose. The blot was probed with BATO 214 and revealed a MW for the naturally occurring *T. gondii* antigen of 24 kDa, while the recombinant antigen has a MW of 29 kDa (see FIG. 5). The leader peptide of the recombinant antigen (mTNF) is about 2 kDa, which explains partly the larger size of the fusion protein. In addition, when the sequence of Tg20 is analyzed for possible eukaryotic cleavage sites (cleaving off signal peptides for secretion), three possible cleavage sites are found between aminoacid positions 17–18, 20–21 and 25–26 (see arrows FIG. 1*b*). Cleavage at one of these positions would reduce the MW of the recombinant to 24, 23.7 or 23.3 kDa, in agreement with the MW of the natural *T. gondii* antigen. The presence of a cysteine residue in the possible signal peptide may explain the formation of a dimer of the fusion protein (see band at about 58 kDa), which is absent in the naturally occurring (cleaved) Tg20 protein.

Example 4. Purification of Recombinant Tg20 Antigen

A 15l fermentation was performed using an induction time of 3 h. The cells were collected by low speed centrifugation and the pellet was stored at $-70°$ C. until further use.

One third of the cell pellet (9 g) was thawed, resuspended in 30 ml lysis buffer (10 mM TrisHcl, 100 mM KCl, 5 mM EDTA. 25 mM $\epsilon$-aminocaproic acid, 1 mM DTT, 1 mM PMSF) and passed twice through the French press. The lysate was centrifuged at 27000 g 30', 4° C. The pellet obtained was then extracted with 20 ml 7 M guanidine chloride, 50 mM phosphate buffer pH7.2. The extract was centrifuged at 27000 g 30', 4° C. The obtained pellet was extracted again with 10 ml of the same buffer. Both extracts were pooled.

An IMAC column was prepared with chelating sepharose fast flow (Pharmacia), activated with $NiCl_2$ as described by the manufacturer, and equilibrated with 6 M guanidinium chloride 50 mM phosphate buffer pH 7.2.

The pooled cell extract (30 ml) was loaded on the column. After washing with running buffer (6 M guanidinium chloride, 50 mM phosphate buffer ph7.2) a step elution was performed with 30, 60 and 100 mM imidazole in running buffer. Eluted fractions (6 ml) were analyzed on SDS-PAGE and WB. The fractions eluting at 100 mM imidazole contained the recombinant Tg20 protein at a purification degree of about 95%. From 5l culture, 36 mg purified protein in 29 ml was thus obtained (1.25 mg/ml) or 7.25 mg/l culture.

The purified recombinant protein showed a clear positive reaction in WB with monoclonal antibodies anti-mTNF and BATO 214 and was further evaluated in ELISA with a panel of sera.

Example 5: Evaluation of Recombinant Tg20 in ELISA.

1. ELISA of Tg20 on G-bank sera.

Optimal conditions for coating Tg20 antigen on ELISA plates were determined as 2 $\mu$g/ml (100 $\mu$l/well) antigen and pH9.5 (carbonate buffer). The serum dilution was $\frac{1}{100}$ and 1% *E. coli* lysate was added to absorb anti- *E. coli* antibodies.

The serum panel (95 positive sera and 43 negative sera) were tested against Tg20 antigen (see table 2). The cutoff value (c.o.) was calculated as the mean O.D. value (x) of the negative sera, plus 3 standard deviations (s.d.), with the mean value being the sum of the individual values divided by the number of values. Sensitivity and specificity of the assay as compared to IF were 79% and 96% respectively.

Furthermore, a correlation was shown between the Immunofluorescence (IF) titre and the sensitivity of the Tg20 ELISA. More Specifically, the Tg20 ELISA showed a sensitivity of 100% for sera with a IF-titre>$\frac{1}{1024}$. For sera with an IF-titre of $\frac{1}{256}$, sensitivity was 85%, while the sensitivity of the Tg20 ELISA reached only 55% for sera with a IF-titre of $\frac{1}{64}$.

2. ELISA of Tg34AR on G-bank sera

The serum samples of the G-bank (95 positive and 43 negative sera) were also tested in ELISA Tg34AR, using the conditions as described by Van Gelder et al. (1993) except for the serum dilution that is now $\frac{1}{100}$. The results obtained are shown in table 2. Sensitivity and specificity of the Tg34AR assay relative to the IF-test are 77% and 98% respectively. Again, the sensitivity was higher for sera with high IF-titre: sera with IF-titre>$\frac{1}{1024}$ were all positive in Tg34AR ELISA (100% while sensitivity was only 89% and 41% for sera with IF-titres of respectively $\frac{1}{256}$ and $\frac{1}{64}$.

3. Combination ELISA with Tg34AR and Tg20

Antigen Tg34AR is usually coated in glycine buffer pH4 (Saavedra et al 1991). The optimal buffer for coating Tg20 antigen is carbonate pH9.5. Several buffers and pH were tested for both antigens, and from this experiment the best compromise for coating both antigens at the same time was determined as carbonate buffer pH 9.5.

Both antigens were diluted in carbonate buffer and coated at concentrations of 6 $\mu$g/ml for Tg34AR and 2 $\mu$g/ml for Tg20. Again 95 positive and 43 negative sera with the G-bank were used to test the ELISA. As described in Example 1, 1% *E. coli* lysate was added to the diluted serum ($\frac{1}{100}$). The results obtained with the individual sera are represented in Table 2. Sensitivity and specificity of this combination ELISA in comparison to the IF test are 92.5% and 98% respectively.

In conclusion, it can thus be said that antigent Tf34AR alone detects 77% of the positive sera in this panel. Tg20 detects 79% of the positive sera. Both antigens combined detect 92.5% of the positive sera and thus partially complement each other.

Example 6: Production of Deletion Clones of Tg20

In order to localize the most important epitopes of the Tg20 antigen, deletion clones were made, expressing only parts of the protein.

Clone Tg20 contained unique restriction sites at positions 585 (StyI), 434 (NaeI) and 287 (Asp700) FIG. 1*a*). The fragments were cut out of pmTNFMPH.Tg20 by digestion with BamHI-StyI (StyI site blunted, BamHI-NaeI and BamHI-Asp700 respectively. The fragments were ligated into vector pIGFH111 or pIGFH10 digested with BamHI-StuI.

The vectors pIGFH111 or pIGFH10 digested with BamHI-StuI.

The vectors pIGFH111 (see FIG. 3) and pIGFH10 (Innogenetics N.V.) are derivatives of pMTNFMPH and have the same basic properties. They contain a larger number of unique restriction sites in the polylinker sequence and the $\epsilon$-enhancer sequence has been inserted in order to give higher expression levels. Plasmid pIGFH10 is the same as pIGHF111 except for the ApaI unique restriction site in the polylinker sequence which is missing in the former.

The principle and protocol to obtain expression of a heterologous gene in pIGFH111 (and pIGFH10) is the same as for pmTNFMPH (described in Example 3). Strain SG4044 [pACI] was used. Three different clones, corresponding to the three different restriction fragments, were tested for expression of the corresponding antigen fragments: Tg20BS (BamHI-StyI), Tg20BN (BamHI - NaeI) and Tg20BA (BamHI - Asp700).

The samples collected from the induction experiments were analysed on Western blots and probed with anti-mouse TNF monoclonal and with BATO 214. All deletion clones reacted with anti-mouse TNF at the expected size, i.e. Tg20BS at approximately 25 kDa, Tg20BN at approximately 20 kDa (with a major degradation band around 15 kDa) and Tg20BA at approximately 14 kDa. Deletion clone Tg20BS gave only very low expression levels. For Tg20BN a lot of "leak" expression was observed, i.e. expression at the non-permissive temperature of 28° C.

When probed with BATO 214 only the two largest deletion clones, i.e. Tg20BS and Tg20BN reacted. This gives a good indication for the position of the BATO 214 epitope on antigen Tg20, i.e. between amino acid position 95 (bp 287) and amino acid position 145 (bp 434) on FIG. 1*b*. Testing with human sera indicates that the main epitopes important in the recognition of human sera are also located in this region (see example 7 and 8).

Clones Tg20BN and Tg20BA were further purified and evaluated in ELISA (see examples 7 and 8). The expression level of clone Tg20BS was too low for purification purposed.

Example 7: Purification of Tg20BN and Evaluation in ELISA

1. Purification of Tg20BN antigent fragment

Tg20BN was purified on IMAC as described above for Tg20 purification, with some modifications. A 151 fermentation was carried out, but growth and expression were carried out at 28° C. only. The "leak" expression level at 28° C. was sufficient for purification purposes and it prevents the more pronounced degradation of the recombinant protein seen at the increased temperature of 42° C. After French press lysis of one cell pellet (51) in lysis buffer (10 mM sodium phosphate, 100 mM KCl, 10 mM $\epsilon$-amino caproic acid), 2 mM PMSF was added. The lysate was centrifuged and the soluble fraction was used for purification.

Guanidinium chloride powder was added to reach a final concentration of 6 M and the solution was centrifuged again. Imidazole was added to reach a concentration of 20 mM. Starting the purification with 20 mM imidazole prevents some *E. coli* contaminants to bind to the column.

An IMAC column was made with chelating sepharose fast flow (Pharmacia), activated with $niCl_2$ as described by the manufacterer, and equilibrated with running buffer (6 M guanidine chloride, 50 mM phosphate, 20 mM imidazole, pH 7.2).

The sample (50 ml) was loaded and after washing with running buffer, a step elution was performed with 35, 50 and 200 mM imidazole in running buffer. Eluted fractions (3 ml) were analysed on WB and SDS-PAGE. The 200 mM fractions contained the recombinant purified protein, that was sufficiently pure (95%). Three fractions (=9 ml) were pooled, the pool containing 230 $\mu$g/ml Tg20BN.

2. ELISA with Tg20BN

ELISA plates were coated with antigen Tg20 and Tg20BN separately at 2 $\mu$g/ml in carbonate buffer. To the sample diluent 1% *E. coli* lysate was added and the serum was diluted 1/100.

Of the G-bank 50 positive (#1 to #50) and 37 negative (#206 to #245 except #221,#228,#233) sera were tested and the results for Tg20 and Tg20BN were compared (see table 3). At a cutoff value of (mean+3 s.d.) no false positives were detected with either test (100% specificity). As to the sensitivity of both assays, the ELISA with the full Tg20 antigen resulted in a sensitivity of 90%, while the truncated protein Tg20BN yielded a sensitivity of 78%.

Most of the sera that are missed by Tg20BN-ELISA are only borderline positive with Tg20-ELISA (see table 3), except for serum #35 and #40 which show a clear drop in reactivity when tested with the deletion clone Tg20BN.

Since the large majority of the sera are still detected by Tg20BN antigen, it can be concluded that the immunodominant epitopes are located on the N-terminal part (aa 1 to aa 145) of the Tg20 antigen. For a few sera (like #35 and #40) an epitope on the C-terminal part seems to be important. These two sera are thus missed by the Tg20BN ELISA, but it is important to note that they are detected by the Tg34AR ELISA (cfr. Table 2).

Example 8: Purification of Tg20BA and Evaluation in ELISA

1. Purification of Tg20BA

The IMAC-purification of Tg20BA was carried out on small scale with Ni-NTA spin columns (Qiagen). A culture of 100 ml MC1061 [pACI] transformed with pIGFH10Tg20BA was induced (42° C.) for 2 h. Cells were harvested and lysed in 6 M guanidinium.HCl, 50 mM phosphate pH 8.3 (shaking for 45 min.). After centrifugation a cleared lysate was obtained and this was loaded on the spin column after the column was equilibrated with the same buffer. The column was washed twice with 6 M guanidiniumHCl, 50 mM phosphate buffer at pH 6.3. Elution was done with 6 M guanidinium.HCl, 50 mM phosphate pH 4.3. This elution step was repeated. The eluates were checked on WB. The first eluate contains most of the purified recombinant protein and is 95% pure. It contained 265 $\mu$g/ml in 600 $\mu$l.

2. ELISA with Tg20BA

From the G-bank 31 sera that gave a positive reaction with Tg20BN were tested on the smaller fragment, Tg20BA, including also 8 negative sera. Tg20BA gave no reaction higher than the cutoff value with these sera (results now shown). This indicates that the Tg20BA fragment (aa pos. 1 to aa pos. 95) does not contain any epitopes important for the recognition of human sera from infected individuals.

From the differential reactivity of antigen fragment Tg20BN and Tg20BA it can be concluded that the main epitope(s) important in the recognition of the humoral immune response are localized in the fragment extending from aa pos. 95 to aa pos. 145, or at least that this region is important for the construction of an immunoreactive epitope.

Further fine mapping of the epitope(s) can be performed using an overlapping set of synthetic peptides.

Example 9: The Combination of Tg34AR and Tg20BN in ELISA

Antigen fragment Tg20 BN was combined in ELISA with Tg34AR to compare the results of this combination ELISA with the results obtained earlier with the combination of Tg20 and Tg34AR (see Table 2). Again, the coating concentration of Tg34AR was 6 $\mu$g/ml and for Tg20BN a concentration of 2 $\mu$g/ml was used. The sensitivity of the combination ELISA with the full size antigen Tg20 (Tg34AR) was only slightly higher (92.5%) as compared to the combination ELISA of the antigen fragment Tg20BN with Tg34AR (sensitivity 91.5%). From this it can be concluded that the most important B-cell epitopes of the Tg20 antigen are located in the Tg20BN-fragment.

Example 10: Localisation of the Dominant Human Epitope on Tg20BN with Peptides

In order to localize the most important B-cell epitope(s) more precisely in the Tg20-BN fragment, a series of overlapping peptides are synthezised, covering the sequence region extending from aminoacid position 95 to amino acid position 145 in FIG. 1b. A biotin molecule was added at the N-terminus during synthesis. The peptides have an overlap of 10 amino acids, and are represented by the following sequences:

GluProAspGluGlnGluGluValHis-PheArgLysArgGlyValArgSerAspAlaGlu (SEQ ID NO 3, aa90–110)

ArgLysArgGlyValArgSerAspAla-GluValThrAspAspAsnIleTyrGluGluHis (SEQ ID NO 4, aa100–120)

ValThrAspAspAsnIleTyrGluGlu-HisThrAspArgLysValValProArgLysSer (SEQ ID NO 5, aa110–130)

ThrAspArgLysValValProAr-gLysSerGluGlyLysArgSerPheLysAspLeuLeu (SEQ ID NO 6, aa120–140)

GluGlyLysArgSerpHeLysAspLeuLeuLysLysLeuAlaLeuPro (SEQ ID NO 7, aa130–146)

Microtiter plates are coated with streptavidin by incubating 100 μl/well of a 5 μg/ml streptavidin solution in carbonate buffer (50 mM, pH 9.6) for 1 h at 37° C. After washing, the biotinylated peptides are added to the wells (100 ng/well, each well (in duplicate) representing a different peptide. Peptides are let to bind the streptavidin for 1 h at 37° C. after which washing occurs. The ELISA procedure is then further continued as described for Tg20 ELISA in Example 1. The five peptides were tested with two positive human sera (18,23), one negative serum (210) and with mouse monoclonal BATO 214 and an unrelated monoclonal (BATO 35). Both monoclonal preparations were dilutions (1/2000) from ascites produced in mice. The conjugate used in the ELISA with the monoclonals was rabbit anti-mouse conjugate (Sigma, dilution 1/5000). The results with the human sera do not indicate one peptide as the more important, all petides react to a greater or smaller extent. Monoclonal BATO 214 reacts with petides SEQ ID NO 3 and SEQ ID NO 4. This probably defines the epitope for BATO 214 between aa 100 and 110.

| | peptide | | | | |
|---|---|---|---|---|---|
| serum | aa90–110 | aa100–120 | aa110–130 | aa120–140 | aa130–146 |
| 18 | .645 | .646 | .840 | .505 | .400 |
| 23 | .517 | .463 | .595 | .764 | .919 |
| 210 | .120 | .120 | .143 | .182 | .212 |
| BATO214 | 1.350 | .2169 | .007 | .009 | .007 |
| BATO35 | .010 | .009 | .010 | .010 | .010 |

Those peptides which seem to contain an important epitope, are further mapped using a set of smaller overlapping peptides (8-mers) tested in the same way as described above.

REFERENCES

Asseline U. Delarue M, Lancelot G, Toulme F, Thuong N (1984) Nucleic acid-binding molecules with high affinity and base sequence specificity:intercalating agents covalently linked to oligodeoxynucleotides. Proc. Natl. Acad. Sci. USA 81(11):3297–301.

Blake M S, Johnston K H, Russell-Jones G J, Gotschlich E C (1984). A rapid, sensitive method for detection of alkaline phosphatase-conjugated anti-antibody on Western blots. Anal. Biochem. 136, 175–179.

Beverly J K A (1976). Toxoplasmosis in animals. Vet. Rec. 99, 123–127.

Blalock J (1990) Complementarity of peptides specified by 'sense' and 'antisense' strands of DNA. Trends Biotechnol. 8: 140–144.

Burg J L, Perelman D, Kasper L H; Ware P L, Boothroyd J C (1988). Molecular analysis of the gene encoding the major surface antigen of Toxoplasma gondii. J. Immunol. 141, 3584–3591.

Buxton D, Thomson K M, Maley S. Wright S, Box H J (1991). Vaccination of sheep with a live incomplete strain (S48) of Toxoplasma gondii and their immunity to challenge when pregnant. Vet. rec. 192, 89–93.

Buxton D, Thomson K M. Maley S. Wright S, Box H J (1993). Experimental challenge of sheep 18 months after vaccination with a live (S48) Toxoplasma gondii vaccine. Vet. rec. 133, 310–312.

Cesbron-Delauw M F, Guy B, Torpier G, Pierce R J, Lenzen G, Cesbron J Y, Charif H, Lepage P, Darcy F, Lecocq J P, Capron, A. (1989). Molecular characterisation of a 23-kilodalton major antigen secreted by Toxoplasma gondii. Proc. Natl. Acad. Sci. USA 86, 7537–-7541.

Compton J (1991). Nucleic acid sequence-based amplification. Nature, 350: 91–92.

de Préval (1978) Immunoglobulins, In: Bach J Immunology, New York, Wiley and Sons: 144–219.

Duck P (1990). Probe amplifier system based on chimeric cycling oligonucleotides. Biotechniques 9, 142–147.

Fleishmann J, Davie J (1984) Immunoglobulins: allotypes and idiotypes. In: Paul W (Ed) Fundamental Immunology, New York, Raven Press: 205–220.

Frenkel J K (1967). Adoptive immunity to intracellular infection. J. Immunol. 98, 1309–1319.

Gazinelli R T, Hakim F T, Hieny S, Shearer G M, Sher A (1991). Synergistic role of CD4+and CD8+T lymphocytes in IFN-y production and protective immunity induced by an attenuated Toxoplasma gondii vaccine. J. Immunol. 146, 286–292.

Gheuens J, Mc Farlin D (1982) Use of monoclonal anti-idiotypic antibody to P3-X6Ag8 myeloma protein for analysis and purification of B lymphocyte hybridoma products. Eur J Immunol 12: 701–703.

Chiso J, Saball E, Leoni J, Rostagno A, Frangio (1990) Binding of cystatin C to C4: the importance of antisense peptides and their interaction. Proc Natl Acad Sci (USA) 87: 1288–1291.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878.

Hughes H P A (1985). Toxoplasmosis: the need for improved diagnostic techniques and accurate risk assessment. Curr. Top. Microbiol. Immunol. 120, 105–139.

Jacobs K, Rudersdorf R, Neill S, Dougherty J, Brown E, Fritsch E (1988). The thermal stability of oligonucleotide duplexes is sequence independent in tetraalkylammoniuim salt solution: application to identifying recombinant DNA clones. Nucl Acids Res 16:4637–4650.

Kwoh D, Davis G, Whitfield K, Chappelle H, Dimichele L, Gingeras T (1989). Transcription-based amplification system and detection of amplified human immunodeficiency virus type 1 with a bead-based sandwich hybridization format. Proc Natl Acad Sci USA, 86: 1173–1177.

Kwok S, Kellogg D, McKinney N, Spasic D, Goda L, Levenson C, Sinisky J, (1990). Effects of primer-template mismatches on the polymerase chain reaction: Human immunodeficiency view type 1 model studies. Nucl. Acids Res., 18:999.

Laemmli U K (1970). Cleavage of structural proteins during the assembly of the head of bacteriophage T4. Nature 227, 680–685.

Landgren U, Kaiser R, Sanders J, Hood L (1988). A ligase-mediated gene detection technique. Science 241:1077–1080.

Lecordier L, Moleon-Borodowsky I, Dubremetz J-F, Tourvielle B, Mercier C, Deslée D, Capron A, Cesbron-Delauw M-F (1995). Characterisation of a dense granule antigen of *Toxoplasma gondii* (GRA6) associated to the network of the parasitophorous vacuole. Mol. Biochem. Parasitol. 70, 85–95.

Lomeli H, Tyagi S, Printchard C, Lisardi P, Kramer F (1989) Quantitative assays based on the use of replicatable hybridization probes. Clin Chem 35: 1826–1831.

McLeod R, Frenkel J K, Estes R G, Mack D G, Eisenhauer P B, Gibori G (1988). Subcutaneous and intestinal vaccination with tachyzoites of *Toxoplasma gondii* and acquisition of immunity to peroral and congenital Toxoplasma challenge. J. Immunol. 140, 1632–1637.

Maniatis, T., E. F. Fritsch, and J. Sambrook. 1982. Molecular cloning. A laboratory manuel. Cold Spring Harbor Laboratory, Cold Spring Harbor, N.Y.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706–10.

Mercier C, Lecordier L, Darcy F, Deslee D, Murray A, Tourvieille B, Maes P, Capron A, Cesbron-Delauw M-F (1993). Molecular characterisation of a dense granule antigen (Gra 2) associated with the parasitophorus vacuole in *Toxoplasma gondii*. Mol. Biochem. Parasitol. 58, 71–82.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23): 5134–43.

Nathan C F, Predergast F J, Wiebe M E, Stanley E R, Platze E, Remold H G, Welte K, Rubin B Y and Murray H W (1984). Activation of human macrophages: comparison of other cytokines with interferon-gamma. J. Exp. Med. 160, 600–605.

Neilsen P, Egholm M, Berg R, Buchardt O (1991) Sequence-selective recognition of DNA by strand displacement with a thymine-substituted polyamide. Science 254(5037): 1497–500.

Neilsen P, Egholm M, Berg R, Buchardt O (1993) Sequence specific inhibition of DNA restriction enzyme cleavage by PNA. Nucleic-Acids-Res. 21(2): 197–200.

Parmley S F, Sgarlato G D, Mark J, Prince J B, Remington J S (1992). Expression, characterisation, and serologic reactivity of recombinant surface antigen P22 of *Toxoplasma gondii*. J. Clin. Microbiol. 30, 1127–1133.

Parmley S F, Sgarlato G D, Remington J S (1993). Genomic and corrected cDNA sequence of the P28 gene from *Toxoplasma gondii*. 57, 161–165.

Perrson M, Caothien R, Burton D (1991) Generation of diverse high affinity human monoclonal antibodies by repertoire cloning. Proc. Natl. Acad. Sci. 88:2432–2436.

Pfefferkorn E R (1984). Interferon gamma blocks the growth of *Toxoplasma gondii* in human fibroblasts by inducing the host cells to degrade tryptophan. Proc. Natl. Acad. Sci. USA 81, 908–912.

Prince J B, Araujo F G, Remington J S, Burg J L, Boothroyd J C, Sharma S D (1989). Cloning of cDNAs encoding a 28 kilodalton antigen of *Toxoplasma gondii*. Mol. Biochem. Parasitol. 34, 3–14.

Remaut E. Tsao H, Fiers W (1983). Improved plasmid vectors with a thermoinducible expression and temperature-regulated runaway replication. Gene 22, 103–113.

Remington J. S. and Krahenbuhl, J. L. (1982) in Immunology of human infection, eds. Nahmias, A. J. and O'Reilly, R. J. (Plenum Publishing, New York), Part II, pp. 327–372.

Roubos E (1990) Sense-antisense complementarity of hormone receptor interaction sites. Trends Biotechnol 8: 279–281.

Saavedra R, De Meuter F, Decourt J-L, Hérion P, (1991). Human T cell clone identifies a potentially protective 54-kDA protein antigen of *Toxoplasma gondii* cloned and expressed in *Escherichia coli*. J. Immunol. 147, 1975–1982.

Saavedra R, De Meuter F, Hérion P, (1990). Monoclonal antibodies identify new *Toxoplasma gondii* soluble antigens. Hybridoma 9, 453–463.

Saiki R, Gelfand D, Stoffel S, Scharf S, Higuchi R, Horn G, Mullis K, Erlich H (1988). Primer-directed enzymatic amplification of DNA with a thermostable DNA polymerase. Science 239:487–491.

Sethi K K, Omata Y, Brandis H, (1985). Contribution of immune interferon (INF-gamma) in lymphokine-induced anti-Toxoplasma activity: studies with recombinant murine IFN-gamma. Immunobiology 170, 270–283.

Sibley L D, Pfefferkorn E R, Boothroyd J C (1991). Proposal for a uniform genetic nomenclature in *Toxoplasma gondii*. Parasitology Today 7, 327–328.

Suzuki Y, Orellana M A, Schreiber R D, Remington J S (1988). Interferon-gamma: the major mediator of resistance against *Toxoplasma gondii*. Science 240, 516–518.

Suzuki Y, Remington J S (1988). Dual regulation of resistance against *Toxoplasma gondii* infection by Lyt-$2^+$ and Lyt-$1^{-30}$ ,L3T$4^+$T cells in mice. J. Immunol. 140, 3943–3946.

Suzuki Y, Remington J S (1990). The effect of anti-IFN-gamma antibody on the protective effect of Lyt-$2^+$ immune T cells against toxoplasmosis in mice. J. Immunol. 144, 1954–1956.

Towbin H, Staehelin T, Gordon J (1979). Eletrophoretic transfer of proteins from polyacrylamide gels to nitrocellulose sheets: procedure and some applications. Proc. Natl. Acad. Sci. USA. 76, 4350–4354.

Van Gelder P, Bosman F, De Meuter F, van Heuverswyn H, and Hérion P (1993). Serodiagnosis of toxoplasmosis by using a recombinant form of the 54- dilodalton rhoptry antigen expressed in *Escherichia coli*. J. Clin Microbiol. 31, 9–15.

Waldeland H, Frenkel J K (1983). Live and killed vaccines against toxoplasmosis in mice. J. Parasitol. 69, 60.

Walker G, Little M, Nadeau J, Shank D (1992). Isothermal in vitro amplification of DNA by a restriction enzyme/DNA polymerase system. Proc Natl Acad Sci USA 89:392–396.

Wu D, Wallace B (1989). The ligation amplification reaction (LAR)—amplification of specific DNA sequences using sequential rounds of template-dependent ligation. Genomics 4:560–569. Barany F (1991). Genetic disease detection and DNA amplification using cloned thermostable ligase. Proc Natl Acad Sci USA 88:189–193.

What is claimed is:

1. A purified and isolated polypeptide or peptide containing a sequence selected from the group consisting of:
   (1) an amino acid sequence extending from an amino acid position x to an amino acid position y in the sequence SEQ ID NO 2,
   wherein x=1 and y=196, or x=1 and y=160, or x=1 and y=145, or x=95 and y=145,
   (2) a fragment of an amino acid sequence of (1), said fragment comprising at least 7 contiguous amino acids from amino acid 96 through amino acid 196 of SEQ ID NO:2, and
   (3) an equivalent of an amino acid sequence of (1) or a fragment of (2) wherein said equivalent comprises said amino acid sequence of (1) or said fragment of (2) wherein at least one amino acid of said sequence or fragment has been replaced by an amino acid as shown in Table 1,
   said polypeptide or peptide containing a reactive epitope which produces at least one of a humoral and a cell-mediated response in a T. gondii infected host organism.

2. A purified and isolated polypeptide or peptide containing a sequence selected from the group consisting of:
   (1) the amino acid sequence extending from an amino acid position 95 to an amino acid position 145 of SEQ ID NO 2,
   (2) a fragment of the amino acid sequence of (1) comprising at least 7 contiguous amino acids from amino acid 96 through amino acid 145 of SEQ ID NO:2,
   (3) at least one of the amino acid sequences represented by GluProAspGluGlnGluGluValHis-PheArgLysArgGlyValArgSerAspAlaGlu (SEQ ID NO 3), or
   ArgLysArgGlyValArgSerAspAla-GluValThrAspAspAsnIleTyrGluGluHis (SEQ ID NO 4), or
   ValThrAspAspAsnIleTyrGluGlu-HisThrAspArgLysValValProArgLysSer (SEQ ID NO 5), or
   ThrAspArgLysValValProAr-gLysSerGluGlyLysArgSerPheLysAspLeuLeu (SEQ ID NO 6), or
   GluGlyLysArgSerPheLysAs-pLeuLeuLysLysLeuAlaLeuPro (SEQ ID NO 7), and
   (4) an equivalent of an amino acid sequence of (1), a fragment of (2) or at least one of the amino acid sequences of (3) wherein said equivalent comprises said amino acid sequence of (1) or said fragment of (2) or said amino acid sequence of (3) wherein at least one amino acid of said sequence or fragment has been replaced by an amino acid as shown in Table 1,
   said polypeptide or peptide containing a reactive epitope which produces at least one of a humoral and a cell-mediated immune response in a T. gondii infected host organism.

3. A fusion protein consisting of a polypeptide or fragment thereof according to claim 1 linked to a heterologous polypeptide sequence.

4. A method for detecting antibodies to T. gondii in a sample, comprising:
   contacting said sample with at least one polypeptide or peptide according to claim 1 under conditions sufficient to form an immunological complex between said polypeptide or peptide and said antibodies, if present, and,
   detecting said immunological complex.

5. A method according to claim 4 wherein said sample is a biological sample from an individual and said method further comprises contacting said sample with at least one further T. gondii polypeptide or peptide for measuring the cellular immune response of said individual.

6. A kit for detecting anti-T. gondii antibodies in a sample, said kit comprising:
   at least one polypeptide or peptide according to claim 1, optionally in combination with other polypeptides or peptides being also optionally immobilized of a solid support,
   optionally, a buffer, or components necessary for producing the buffer, enabling a binding reaction to occur between the antibodies present in said sample and said polypeptides or peptides,
   optionally, a means for detecting the immune complex formed, and,
   optionally, an automated scanning and interpretation device for inferring the presence of said antibodies in said sample.

7. A kit according to claim 6, further comprising at least one non-T. gondii pathogen-specific detection reactant selected from the group consisting of a non-T. gondii, pathogen-specific, polypeptide, antibody and polynucleic acid.

8. A purified and isolated polypeptide or peptide according to claim 1 containing a sequence selected from the group consisting of:
   (1) an amino acid sequence extending from an amino acid position x to an amino acid position y in the sequence SEQ ID NO:2,
   wherein x=1 and y=196, or x=1 and y=160, or x=1 and y=145, or x=95 and y=145, and
   (2) a fragment of an amino acid sequence of (1), said fragment comprising at least 7 contiguous amino acids from amino acid 96 through amino acid 196 of SEQ ID NO:2,
   said polypeptide or peptide containing a reactive epitope which produces at least one of a hundred and a cell-mediated response in a T. gondii infected host organism.

9. A purified and isolated polypeptide or peptide according to claim 2 containing a sequence selected from the group consisting of:
   (1) the amino acid sequence extending from an amino acid position 95 to an amino acid position 145 of SEQ ID NO:2,
   (2) a fragment of the amino acid sequence of (1) comprising at least 7 contiguous amino acids from amino acid 96 through amino acid 145 of SEQ ID NO:2, (3) at least one of the amino acid sequences represented by GluProAspGluGlnGluGluValHisPheArgLysArgGlyValArgSerAspAlaGlu (SEQ ID NO 3), or ArgLysArgGlyValArgSerAspAlaGluValThrAspAspAsnIleTyrGluGluHis (SEQ ID NO 4), or ValThrAspAspAsnIleTyrGluGluHisThrAspArgLysValValProArgLysSer (SEQ ID NO 5), or ThrAspArgLysValValProArgLysSerGluGlyLysArgSerPheLysAspLeuLeu (SEQ ID NO 6), or GluGlyLysArgSerPheLysAspLeuLeuLysLysLeuAlaLeuPro (SEQ ID NO 7), and said polypeptide or peptide containing a reactive epitope which produces at least one of a humoral and a cell-mediated immune response in a *T. gondii* infected host organism.

10. A purified and isolated polypeptide or peptide according to claim 2 containing a sequence selected from the group consisting of:

(1) the amino acid sequence extending from an amino acid position 95 to an amino acid position 145 of SEQ ID NO:2, and (2) a fragment of the amino acid sequence of (1) comprising at least 7 contiguous amino acids from amino acid 96 through amino acid 145 of SEQ ID NO:2, said polypeptide or peptide containing a reactive epitope which produces at least one of a humoral and a cell-mediated immune response in a *T. gondii* infected host organism.

11. A fusion protein comprising a polypeptide or peptide according to claim 1, linked to a heterologous polypeptide sequence.

12. A fusion protein comprising a polypeptide or peptide according to claim 2, linked to a heterologous polypeptide sequence.

13. A fusion protein comprising a polypeptide or peptide according to claim 8, linked to a heterologous polypeptide sequence.

14. A fusion protein comprising a polypeptide or peptide according to claim 9, linked to a heterologous polypeptide sequence.

15. A fusion protein comprising a polypeptide or peptide according to claim 10, linked to a heterologous polypeptide sequence.

16. A method of detecting antibodies to *T. gondii* in a sample comprising contacting said sample with at least one polypeptide or peptide according to claim 2 under conditions sufficient to form an immunological complex between said polypeptide or peptide and said antibodies, if present, and detecting said immunological complex.

17. A method of detecting antibodies to *T. gondii* in a sample comprising contacting said sample with at least one polypeptide or peptide according to claim 8 under conditions sufficient to form an immunological complex between said polypeptide or peptide and said antibodies, if present, and detecting said immunological complex.

18. A method of detecting antibodies to *T. gondii* in a sample comprising contacting said sample with at least one polypeptide or peptide according to claim 9 under conditions sufficient to form an immunological complex between said polypeptide or peptide and said antibodies, if present, and detecting said immunological complex.

19. A method of detecting antibodies to *T. gondii* in a sample comprising contacting said sample with at least one polypeptide or peptide according to claim 10 under conditions sufficient to form an immunological complex between said polypeptide or peptide and said antibodies, if present, and detecting said immunological complex.

20. The method of claim 16 wherein said sample is a biological sample from an individual and said method further comprises contacting said sample with at least one further *T. gondii* polypeptide or peptide for measuring the cellular immune response of said individual.

21. The method of claim 17 wherein said sample is a biological sample from an individual and said method further comprises contacting said sample with at least one further *T. gondii* polypeptide or peptide for measuring the cellular immune response of said individual.

22. The method of claim 18 wherein said sample is a biological sample from an individual and said method further comprises contacting said sample with at least one further *T. gondii* polypeptide or peptide for measuring the cellular immune response of said individual.

23. The method of claim 19 wherein said sample is a biological sample from an individual and said method further comprises contacting said sample with at least one further *T. gondii* polypeptide or peptide for measuring the cellular immune response of said individual.

24. A kit for detecting anti-*T. gondii* antibodies in a sample, said kit comprising:

at least one polypeptide or peptide according to claim 2, optionally in combination with other polypeptides or peptides being also optionally immobilized of a solid support, optionally, a buffer, or components necessary for producing the buffer, enabling a binding reaction to occur between the antibodies present in said sample and said polypeptide or peptide, optionally, a means for detecting the immune complex formed, and, optionally, an automated scanning and interpretation device for inferring the presence of said antibodies in said sample.

25. A kit for detecting anti-*T. gondii* antibodies in a sample, said kit comprising:

at least one polypeptide or peptide according to claim 8, optionally in combination with other polypeptides or peptides being also optionally immobilized of a solid support, optionally, a buffer, or components necessary for producing the buffer, enabling a binding reaction to occur between the antibodies present in said sample and said polypeptide or peptide, optionally, a means for detecting the immune complex formed, and, optionally, an automated scanning and interpretation device for inferring the presence of said antibodies in said sample.

26. A kit for detecting anti-*T. gondii* antibodies in a sample, said kit comprising:

at least one polypeptide or peptide according to claim 9, optionally in combination with other polypeptides or peptides being also optionally immobilized of a solid support, optionally, a buffer, or components necessary for producing the buffer, enabling a binding reaction to occur between the antibodies present in said sample and said polypeptide or peptide, optionally, a means for detecting the immune complex formed, and, optionally, an automated scanning and interpretation device for inferring the presence of said antibodies in said sample.

27. A kit for detecting anti-*T. gondii* antibodies in a sample, said kit comprising:

at least one polypeptide or peptide according to claim 10, optionally in combination with other polypeptides or peptides being also optionally immobilized of a solid support, optionally, a buffer, or components necessary for producing the buffer, enabling a binding reaction to occur between the antibodies present in said sample and said polypeptide or peptide, optionally, a means for detecting the immune complex formed, and, optionally, an automated scanning and interpretation device for inferring the presence of said antibodies in said sample.

28. A kit according to claim 24, further comprising at least one non-*T. gondii* pathogen-specific detection reactant selected from the group consisting of a non-*T. gondii*, pathogen-specific, polypeptide, antibody and polynucleic acid.

29. A kit according to claim 25, further comprising at least one non-*T. gondii* pathogen-specific detection reactant selected from the group consisting of a non-*T. gondii*, pathogen-specific, polypeptide, antibody and polynucleic acid.

30. A kit according to claim 26, further comprising at least one non-*T. gondii* pathogen-specific detection reactant selected from the group consisting of a non-*T. gondii*, pathogen-specific, polypeptide, antibody and polynucleic acid.

31. A kit according to claim 27, further comprising at least one non-*T. gondii* pathogen-specific detection reactant selected from the group consisting of a non-*T. gondii*, pathogen-specific, polypeptide, antibody and polynucleic acid.

* * * * *